(12) United States Patent
Griffin et al.

(10) Patent No.: US 7,881,797 B2
(45) Date of Patent: Feb. 1, 2011

(54) METHODS AND DEVICES FOR GASTROINTESTINAL STIMULATION

(75) Inventors: Bobby Griffin, Golden Valley, MN (US); Mitchell Dann, Wilson, WY (US); Greg Fluet, Jackson, WY (US)

(73) Assignee: ValenTx, Inc., Carpinteria, CA (US)

( * ) Notice: Subject to any disclaimer, the term of this patent is extended or adjusted under 35 U.S.C. 154(b) by 847 days.

(21) Appl. No.: 11/789,561

(22) Filed: Apr. 25, 2007

(65) Prior Publication Data

US 2008/0058887 A1 Mar. 6, 2008

Related U.S. Application Data

(60) Provisional application No. 60/794,772, filed on Apr. 25, 2006.

(51) Int. Cl.
*A61M 5/00* (2006.01)
*A61B 17/08* (2006.01)

(52) U.S. Cl. .......................... 607/40; 604/264; 606/151
(58) Field of Classification Search .................. 607/40; 604/264, 270, 500
See application file for complete search history.

(56) References Cited

U.S. PATENT DOCUMENTS

| | | | |
|---|---|---|---|
| 3,589,356 A | 6/1971 | Silverman |
| 3,982,544 A | 9/1976 | Dyck |
| 4,006,747 A | 2/1977 | Kronenthal et al. |
| 4,043,345 A | 8/1977 | Kramann et al. |
| 4,109,659 A | 8/1978 | Sheridan |
| 4,134,405 A | 1/1979 | Smit |
| 4,217,664 A | 8/1980 | Faso |
| 4,235,238 A | 11/1980 | Ogiu et al. |
| 4,252,131 A | 2/1981 | Hon et al. |
| 4,271,839 A | 6/1981 | Fogarty et al. |
| 4,315,509 A | 2/1982 | Smit |
| 4,329,995 A | 5/1982 | Anthracite |
| 4,501,264 A | 2/1985 | Rockey |
| 4,532,926 A | 8/1985 | O'Holla |
| 4,606,347 A | 8/1986 | Fogarty et al. |
| 4,630,609 A | 12/1986 | Chin |
| 4,641,653 A | 2/1987 | Rockey |
| 4,719,916 A | 1/1988 | Ravo |

(Continued)

OTHER PUBLICATIONS

Antireflux operations at flexible endoscopy using endoluminal stitching techniques: an experimental study, Sritharan S. Kadirkamanathan et al., *Gastrointestinal Endoscopy*, vol. 44, No. 2, 1995 pp. 133-143.

(Continued)

*Primary Examiner*—Carl H. Layno
*Assistant Examiner*—Jon-Eric C. Morales
(74) *Attorney, Agent, or Firm*—Knobbe, Martens, Olson & Bear LLP

(57) ABSTRACT

Methods and devices for gastrointestinal stimulation are disclosed. In one embodiment, disclosed is an electrical stimulator device that includes a circuit board and a battery contained within a base housing; a conduction element; and at least one electrode. In some embodiments, the stimulator base housing can be directly attached to a wall of a body lumen. In other embodiments, the stimulator base housing can be attached to a cuff or a sleeve device. In still other embodiments, one or more elements of the system are free-floating within the GI tract. The devices can be delivered endoscopically, and in some embodiments toposcopically.

20 Claims, 21 Drawing Sheets

U.S. PATENT DOCUMENTS

| | | | |
|---|---|---|---|
| 4,763,653 A | 8/1988 | Rockey | |
| 4,846,836 A | 7/1989 | Reich | |
| 4,863,440 A | 9/1989 | Chin | |
| 4,905,693 A | 3/1990 | Ravo | |
| 4,946,440 A | 8/1990 | Hall | |
| 5,085,661 A | 2/1992 | Moss | |
| RE34,021 E | 8/1992 | Mueller et al. | |
| 5,171,305 A | 12/1992 | Schickling et al. | |
| 5,236,423 A | 8/1993 | Mix et al. | |
| 5,306,300 A | 4/1994 | Berry | |
| 5,314,473 A | 5/1994 | Godin | |
| 5,411,508 A | 5/1995 | Bessler et al. | |
| 5,431,666 A | 7/1995 | Sauer et al. | |
| 5,458,573 A | 10/1995 | Summers | |
| 5,470,337 A | 11/1995 | Moss | |
| 5,582,616 A | 12/1996 | Bolduc et al. | |
| 5,645,568 A | 7/1997 | Chervitz et al. | |
| 5,676,688 A | 10/1997 | Jaker et al. | |
| 5,785,684 A | 7/1998 | Zimmon | |
| 5,820,584 A | 10/1998 | Crabb | |
| 5,824,008 A | 10/1998 | Bolduc et al. | |
| 5,843,164 A | 12/1998 | Frantzen | |
| 5,861,036 A | 1/1999 | Godin | |
| 5,887,594 A | 3/1999 | LoCicero, III | |
| 5,957,940 A | 9/1999 | Tanner et al. | |
| 5,972,023 A | 10/1999 | Tanner et al. | |
| 5,997,556 A | 12/1999 | Tanner | |
| 6,113,609 A | 9/2000 | Adams | |
| 6,193,733 B1 | 2/2001 | Adams | |
| 6,254,642 B1 | 7/2001 | Taylor | |
| 6,264,700 B1 | 7/2001 | Kilcoyne et al. | |
| 6,285,897 B1 | 9/2001 | Kilcoyne et al. | |
| 6,312,437 B1 | 11/2001 | Kortenbach | |
| 6,338,345 B1 | 1/2002 | Johnson et al. | |
| 6,387,104 B1 | 5/2002 | Pugsley, Jr. et al. | |
| 6,409,656 B1 | 6/2002 | Sangouard et al. | |
| 6,447,533 B1 | 9/2002 | Adams | |
| 6,494,888 B1 | 12/2002 | Laufer et al. | |
| 6,520,974 B2 | 2/2003 | Tanner et al. | |
| 6,535,764 B2 | 3/2003 | Imran et al. | |
| 6,544,291 B2 | 4/2003 | Taylor | |
| 6,558,400 B2 | 5/2003 | Deem et al. | |
| 6,558,429 B2 | 5/2003 | Taylor | |
| 6,592,596 B1 | 7/2003 | Geitz | |
| 6,595,911 B2 | 7/2003 | LoVuolo | |
| 6,626,916 B1 | 9/2003 | Yeung et al. | |
| 6,626,919 B1 | 9/2003 | Swanstrom | |
| 6,635,066 B2 | 10/2003 | Tanner et al. | |
| 6,675,809 B2 | 1/2004 | Stack et al. | |
| 6,699,263 B2 | 3/2004 | Cope | |
| 6,702,735 B2 | 3/2004 | Kelly | |
| 6,736,828 B1 | 5/2004 | Adams et al. | |
| 6,740,121 B2 | 5/2004 | Geitz | |
| 6,746,489 B2 | 6/2004 | Dua et al. | |
| 6,764,518 B2 | 7/2004 | Godin | |
| 6,773,452 B2 | 8/2004 | Shaker | |
| 6,790,237 B2 | 9/2004 | Stinson | |
| 6,845,776 B2 | 1/2005 | Stack et al. | |
| 6,946,002 B2 | 9/2005 | Geitz | |
| 6,994,095 B2 | 2/2006 | Burnett et al. | |
| 7,025,791 B2 | 4/2006 | Levine et al. | |
| 7,037,344 B2 | 5/2006 | Kagan et al. | |
| 7,097,665 B2 | 8/2006 | Stack et al. | |
| 7,111,627 B2 | 9/2006 | Stack et al. | |
| 7,120,498 B2 | 10/2006 | Imran et al. | |
| 7,121,283 B2 | 10/2006 | Stack et al. | |
| 7,122,058 B2 | 10/2006 | Levine et al. | |
| 7,146,984 B2 | 12/2006 | Stack et al. | |
| 7,152,607 B2 | 12/2006 | Stack et al. | |
| 7,160,312 B2 | 1/2007 | Saadat | |
| 7,175,669 B2 | 2/2007 | Geitz | |
| RE39,533 E | 3/2007 | Ranoux | |
| 7,211,114 B2 | 5/2007 | Bessler | |
| 7,220,237 B2 | 5/2007 | Gannoe et al. | |
| 7,220,284 B2 | 5/2007 | Kagan et al. | |
| 7,229,428 B2 | 6/2007 | Gannoe et al. | |
| 7,244,270 B2 | 7/2007 | Lesh | |
| 7,267,694 B2 | 9/2007 | Levine et al. | |
| 7,288,099 B2 | 10/2007 | Deem et al. | |
| 7,288,101 B2 | 10/2007 | Deem et al. | |
| 7,306,614 B2 | 12/2007 | Weller et al. | |
| 7,309,341 B2 | 12/2007 | Ortiz et al. | |
| 7,314,489 B2 | 1/2008 | McKenna et al. | |
| 7,316,716 B2 | 1/2008 | Egan | |
| 7,329,285 B2 | 2/2008 | Levine et al. | |
| 7,338,505 B2 | 3/2008 | Belson | |
| 7,347,875 B2 | 3/2008 | Levine et al. | |
| 7,354,454 B2 | 4/2008 | Stack et al. | |
| 7,371,215 B2 | 5/2008 | Colliou et al. | |
| 7,431,725 B2 | 10/2008 | Stack et al. | |
| 7,468,060 B2 | 12/2008 | Utley et al. | |
| 7,476,256 B2 | 1/2009 | Meade et al. | |
| 7,483,754 B2 | 1/2009 | Imran et al. | |
| 7,509,175 B2 | 3/2009 | Sparks et al. | |
| 7,520,884 B2 | 4/2009 | Swanstrom et al. | |
| 7,666,180 B2 | 2/2010 | Viola et al. | |
| 7,753,870 B2 | 7/2010 | Demarais et al. | |
| 7,780,592 B2 | 8/2010 | Tronnes | |
| 7,794,447 B2 | 9/2010 | Dann et al. | |
| 2001/0044595 A1 | 11/2001 | Reydel et al. | |
| 2001/0056282 A1 | 12/2001 | Sonnenschein et al. | |
| 2002/0016607 A1 | 2/2002 | Bonadio et al. | |
| 2002/0026214 A1 | 2/2002 | Tanner et al. | |
| 2002/0035370 A1 | 3/2002 | Kortenbach | |
| 2002/0040226 A1 | 4/2002 | Laufer et al. | |
| 2002/0058960 A1 | 5/2002 | Hudson et al. | |
| 2002/0082621 A1 | 6/2002 | Schurr et al. | |
| 2002/0111658 A1 | 8/2002 | Greenberg et al. | |
| 2002/0165589 A1 | 11/2002 | Imran et al. | |
| 2002/0183768 A1 | 12/2002 | Deem et al. | |
| 2002/0188354 A1 | 12/2002 | Peghini | |
| 2003/0014064 A1 | 1/2003 | Blatter | |
| 2003/0018358 A1 | 1/2003 | Saadat | |
| 2003/0040804 A1 | 2/2003 | Stack et al. | |
| 2003/0040808 A1 | 2/2003 | Stack et al. | |
| 2003/0055313 A1 | 3/2003 | Anderson et al. | |
| 2003/0055442 A1 | 3/2003 | Laufer et al. | |
| 2003/0065340 A1 | 4/2003 | Geitz | |
| 2003/0120285 A1 | 6/2003 | Kortenbach | |
| 2003/0130560 A1 | 7/2003 | Suzuki et al. | |
| 2003/0139752 A1 | 7/2003 | Pasricha et al. | |
| 2003/0181929 A1 | 9/2003 | Geitz | |
| 2003/0191497 A1 | 10/2003 | Cope | |
| 2003/0208209 A1 | 11/2003 | Gambale et al. | |
| 2004/0002734 A1 | 1/2004 | Fallin et al. | |
| 2004/0024427 A1 | 2/2004 | Imran et al. | |
| 2004/0044364 A1 | 3/2004 | DeVries et al. | |
| 2004/0059349 A1 | 3/2004 | Sixto, Jr. et al. | |
| 2004/0059354 A1 | 3/2004 | Smith | |
| 2004/0087976 A1 | 5/2004 | DeVries et al. | |
| 2004/0087977 A1 | 5/2004 | Nolan et al. | |
| 2004/0092892 A1* | 5/2004 | Kagan et al. ................ 604/264 | |
| 2004/0093065 A1 | 5/2004 | Yachia et al. | |
| 2004/0097986 A1 | 5/2004 | Adams | |
| 2004/0097987 A1 | 5/2004 | Pugsley et al. | |
| 2004/0102855 A1 | 5/2004 | Shank | |
| 2004/0116949 A1 | 6/2004 | Ewers et al. | |
| 2004/0117031 A1 | 6/2004 | Stack et al. | |
| 2004/0122453 A1 | 6/2004 | Deem et al. | |
| 2004/0122456 A1 | 6/2004 | Saadat et al. | |
| 2004/0122473 A1 | 6/2004 | Ewers et al. | |
| 2004/0133089 A1 | 7/2004 | Kilcoyne et al. | |
| 2004/0133147 A1 | 7/2004 | Woo | |
| 2004/0133219 A1 | 7/2004 | Forsell | |

| | | |
|---|---|---|
| 2004/0133238 A1 | 7/2004 | Cerier |
| 2004/0138525 A1 | 7/2004 | Saadat et al. |
| 2004/0138529 A1 | 7/2004 | Wiltshire et al. |
| 2004/0138761 A1 | 7/2004 | Stack et al. |
| 2004/0143342 A1 | 7/2004 | Stack et al. |
| 2004/0147958 A1 | 7/2004 | Lam et al. |
| 2004/0162567 A9 | 8/2004 | Adams |
| 2004/0162568 A1 | 8/2004 | Saadat et al. |
| 2004/0167546 A1 | 8/2004 | Saadat et al. |
| 2004/0181242 A1 | 9/2004 | Stack et al. |
| 2004/0186514 A1 | 9/2004 | Swain et al. |
| 2004/0193190 A1 | 9/2004 | Luddicoat et al. |
| 2004/0199189 A1 | 10/2004 | Gifford et al. |
| 2004/0220682 A1 | 11/2004 | Levine et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0243195 A1 | 12/2004 | Imran et al. |
| 2004/0249362 A1 | 12/2004 | Levine et al. |
| 2004/0249367 A1 | 12/2004 | Saadat et al. |
| 2005/0033240 A1 | 2/2005 | Oishi et al. |
| 2005/0033331 A1 | 2/2005 | Burnett et al. |
| 2005/0049718 A1 | 3/2005 | Dann et al. |
| 2005/0065401 A1 | 3/2005 | Saadat et al. |
| 2005/0075653 A1 | 4/2005 | Saadat et al. |
| 2005/0075654 A1 | 4/2005 | Kelleher |
| 2005/0080431 A1 | 4/2005 | Levine et al. |
| 2005/0080444 A1 | 4/2005 | Kraemer et al. |
| 2005/0085787 A1 | 4/2005 | Laufer |
| 2005/0085900 A1 | 4/2005 | Case et al. |
| 2005/0096750 A1 | 5/2005 | Kagan et al. |
| 2005/0101977 A1 | 5/2005 | Gannoe |
| 2005/0125020 A1 | 6/2005 | Meade et al. |
| 2005/0143784 A1 | 6/2005 | Imran |
| 2005/0177181 A1* | 8/2005 | Kagan et al. .............. 606/151 |
| 2005/0187567 A1 | 8/2005 | Baker et al. |
| 2005/0192629 A1 | 9/2005 | Saadat et al. |
| 2005/0197714 A1 | 9/2005 | Sayet |
| 2005/0197715 A1 | 9/2005 | Kugler et al. |
| 2005/0203547 A1 | 9/2005 | Weller et al. |
| 2005/0222592 A1 | 10/2005 | Gannoe et al. |
| 2005/0228413 A1 | 10/2005 | Binmoeller et al. |
| 2005/0228504 A1 | 10/2005 | Demerais |
| 2005/0247320 A1 | 11/2005 | Stack et al. |
| 2005/0261549 A1 | 11/2005 | Hewit et al. |
| 2005/0261712 A1 | 11/2005 | Balbierz et al. |
| 2005/0267499 A1 | 12/2005 | Stack et al. |
| 2005/0267595 A1 | 12/2005 | Chen et al. |
| 2006/0009858 A1 | 1/2006 | Levine et al. |
| 2006/0015125 A1 | 1/2006 | Swain et al. |
| 2006/0020164 A1 | 1/2006 | Butler et al. |
| 2006/0020247 A1 | 1/2006 | Kagan et al. |
| 2006/0020254 A1 | 1/2006 | von Hoffmann |
| 2006/0020277 A1 | 1/2006 | Gostout et al. |
| 2006/0020278 A1 | 1/2006 | Burnett et al. |
| 2006/0025819 A1 | 2/2006 | Nobis et al. |
| 2006/0047289 A1 | 3/2006 | Fogel |
| 2006/0064120 A1 | 3/2006 | Levine et al. |
| 2006/0074458 A1 | 4/2006 | Imran |
| 2006/0155312 A1 | 7/2006 | Levine et al. |
| 2006/0155375 A1 | 7/2006 | Kagan et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0173422 A1 | 8/2006 | Reydel et al. |
| 2006/0206063 A1 | 9/2006 | Kagan et al. |
| 2006/0206064 A1 | 9/2006 | Kagan et al. |
| 2006/0217762 A1 | 9/2006 | Maahs et al. |
| 2006/0235446 A1 | 10/2006 | Godin |
| 2006/0247718 A1* | 11/2006 | Starkebaum .............. 607/40 |
| 2006/0253126 A1 | 11/2006 | Bjerken et al. |
| 2006/0264982 A1 | 11/2006 | Viola et al. |
| 2006/0265021 A1* | 11/2006 | Herbert et al. .............. 607/40 |
| 2006/0265082 A1 | 11/2006 | Meade et al. |
| 2006/0287734 A1 | 12/2006 | Stack et al. |
| 2006/0293742 A1 | 12/2006 | Dann et al. |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0010865 A1 | 1/2007 | Dann et al. |
| 2007/0010866 A1 | 1/2007 | Dann et al. |
| 2007/0016244 A1 | 1/2007 | Behl et al. |
| 2007/0027548 A1 | 2/2007 | Levine et al. |
| 2007/0027549 A1 | 2/2007 | Godin |
| 2007/0032879 A1 | 2/2007 | Levine et al. |
| 2007/0083271 A1 | 4/2007 | Levine et al. |
| 2007/0100367 A1 | 5/2007 | Quijano et al. |
| 2007/0106233 A1 | 5/2007 | Huang et al. |
| 2007/0106313 A1 | 5/2007 | Golden et al. |
| 2007/0129719 A1 | 6/2007 | Kendale et al. |
| 2007/0156248 A1 | 7/2007 | Marco et al. |
| 2007/0198074 A1 | 8/2007 | Dann et al. |
| 2007/0208360 A1 | 9/2007 | Demarais et al. |
| 2007/0219571 A1 | 9/2007 | Balbierz et al. |
| 2007/0225555 A1 | 9/2007 | Stefanchik |
| 2007/0233162 A1 | 10/2007 | Gannoe et al. |
| 2007/0293885 A1 | 12/2007 | Binmoeller |
| 2008/0004606 A1 | 1/2008 | Swain et al. |
| 2008/0009888 A1 | 1/2008 | Ewers et al. |
| 2008/0033574 A1 | 2/2008 | Bessler et al. |
| 2008/0058840 A1 | 3/2008 | Albrecht et al. |
| 2008/0103604 A1 | 5/2008 | Levine et al. |
| 2008/0167606 A1 | 7/2008 | Dann et al. |
| 2008/0167610 A1 | 7/2008 | Dann et al. |
| 2008/0167629 A1 | 7/2008 | Dann et al. |
| 2008/0195226 A1 | 8/2008 | Williams et al. |
| 2008/0208355 A1 | 8/2008 | Stack et al. |
| 2008/0208356 A1 | 8/2008 | Stack et al. |
| 2008/0208357 A1 | 8/2008 | Melanson et al. |
| 2008/0221597 A1 | 9/2008 | Wallace et al. |
| 2008/0228030 A1 | 9/2008 | Godin |
| 2008/0243071 A1 | 10/2008 | Quijano et al. |
| 2008/0249533 A1 | 10/2008 | Godin |
| 2008/0255587 A1 | 10/2008 | Cully et al. |
| 2008/0255594 A1 | 10/2008 | Cully et al. |
| 2008/0255678 A1 | 10/2008 | Cully et al. |
| 2008/0269797 A1 | 10/2008 | Stack et al. |
| 2009/0012356 A1 | 1/2009 | Dann et al. |
| 2009/0012541 A1 | 1/2009 | Dahl et al. |
| 2009/0012544 A1 | 1/2009 | Thompson et al. |
| 2009/0012553 A1 | 1/2009 | Swain et al. |
| 2009/0062881 A1 | 3/2009 | Gross |

OTHER PUBLICATIONS

Endoscopic suturing, C. Paul Swain MD, *Balliere's Clinical Gastroenterology*, vol. 13, No. 1. pp. 97-108, 1999.

Progression rate of self-propelled feeding tubes in critically ill patients, Mette M. Berger et al., *Intensive Care Med* Oct. 29, 2002, pp. 1768-1774.

Iatrogenic Intussusception: a Complication of Long Intestinal Tubes, Patricia Redmond, M.D., et al., *American Jounal of Gastroenterology*, vol. 77, No. 1, 1982, pp. 39-42.

Design and Testing of a New, Small Diameter, Single Stitch Endoscopic Sewing Machine, C.P. Swain et al., *Abstracts Submitted to A/S/G/E/ 1990*, Vo. 36, No. 2, 1990, pp. 213, 214.

Endoscopic Suturing of a Novel Gastroesophageal Antireflux Device (GARD) A Preliminary Report, N.J. Godin et al., *Gastrointestinal Endoscopy*, vol. 43, No. 4, 1996.

An endoscopic stapling device: the development of new flexible endoscopically controlled device for placing multiple transmural staples in gastrointestinal tissue, C. Paul Swain, MD et al., *Gastrointestinal Endoscopy*, vol. 35, No. 4, 1989 pp. 338-339.

An endoscopically deliverable tissue-transfixing device for securing biosensors in the gastrointestinal tract, C. Paul Swain, MD et al. *Gastrointestinal Endoscopy*, 1994 vol. 40 No. 6 pp. 730-734.

Development of a gastroplasty with variable diameter. Experimental study using artificial sphincters, M. Merlini et al., 1992 Abstract.

Synthetic Biodegradable Polymers as Medical Devices, John C. Middleton et al., *Medical Plastics and Biomaterials Magazine MPS Article Index*, Mar. 1998.

Experimental study on in situ tissue engineering of the stomach by an acellular collagen sponge scaffold graft, Hori Y. Nakamura et al., Abstract, May 2001.

Repair of Full-Thickness Defects in Alimentary Tract Wall with Patches of Expanded Polytetrafluoroethylene, Daniel S. Oh, MD et al., Annals of Surgery 2002; 235:708-712.

Stents in the small intestine, Singh S, Gagneja HK, Abstract, Oct. 2002.

Endoscopic vertical band gastroplasty with an endoscopic sewing machine, Amjad N. Awan MD et al., *Gastrointestinal Endoscopy*, vol. 55, No. 2, 2002, pp. 254-256.

A through-the-scope device of suturing and tissue approximation under EUS control, Annette Fritscher-Ravens, MD, et al., *Gastrointestinal Endoscopy*, vol. 56, No. 5, 2002, pp. 737-742.

Evaluation of porcine-derived small intestine submucosa as a biodegradable graft for gastrointestinal healing, SG del la Fuente et al., Abstract, J. Gastrointest Surg Jan. 2003.

Bard EndoCinch: the device, the technique and pre-clinical studies, Paul Swain, M.D. et al., *Gastrointestinal Endoscopy Clinics of North America*, 13, 2003 pp. 75-88.

Endoscopic suturing for gastroesophageal reflux disease: clinical outcome with the Bard Endocinch, Richard I: Rothstein, MD et al., *Gastrointestinal Endoscopy Clinics of North America*, 13 (2003) pp. 89-101.

Wilson-Cook sewing device: the device, technique, and preclinical studies, Michael Rosen MD, et al., *Gastrointestinal Endoscopy Clinics of North America*, 13 (2003) pp. 103-108.

Endoscopic full-thickness plication: the device, technique, pre-clinical and early clinical experience, Ram Chuttani, MD, *Gastrointestinal Endoscopy Clinics of North America*, 13 (2003) pp. 109-116.

Microvasive gastric stapler: the device, technique, and preclinical results, Tom R. De Meester MD, *Gastrointestinal Endoscopy Clinics of North America*, 13 (2003) pp. 117-133.

Endoscopic Gastropexy and Crural Repair for Gastro-Esophageal Reflux: Transgastric Surgery Under Endoscopic Ultrasound Control II, Anette Fritscher-Ravens et al. *Digestive Disease Week* 2003 Abstract.

Endoscopic suturing for treatment of GERD, m. Brian Fennerty, MD, *Gastrointestinal Endoscopy*, vol. 57, No. 3, 2003 pp. 390-395.

Transgastric gastropexy and hiatal hernia repair for GERD under EUS control: a porcine model, Annette Fritscher-Ravens, MD et al., *Gastrointestinal Endoscopy*, vol. 59, No. 1, 2004, pp. 89-95.

Effect of Duodenal-Jejunal Exclusion of a Non-obese Animal Model of Type 2 Diabetes, Francesco Rubino, MD et al., *Annals of Surgery*, vol. 239, No. 1, Jan. 2004, p.

The Lap-Band Solution, BioEnterics Corporation, Brochurehttp://www.bioenterics.com/.

Successful Uses in Approximation Ligation & Fixation using the Quik-Stitch, Endoscopic Suturing System, Paré Surgical, Inc. Brochure 2001.

Obesity Treatment, Medical Innovation Development, Brochure.

The Remote Controlled Swedish Band, The method of choice in modern treatment of morbid obesity, Obtech Medical AG, Brochure.

The Bard EndoCinch Procedure, Introducing Endoscopic Technology for the Treatment of GERD.

Microvasive Wallstent® Colonic and Duodenal Endoprosthesis, Boston Scientific website, www.bostonscientific.com, Sep. 20, 2002.

Cook® Wilson-Cook Medical GI Endoscopy, Wilson Cook: Biliary/Pancreatic Stents, www.cookgroup.com, Sep. 20, 2002.

ROSS.COM, Abbott Laboratories Online, Product Handbook, T-Fastener Set.

T=Anchor Introducer Gun™ Details, Moss™ Tubes Brochure.

Bioabsorable Polymers, William B. Gleason, *University of Minnesota*, 1998.

*Cope Gastrointestinal Suture Anchor Set*, www.cookgroup.com, *Cook Diagnostic and Interventional Products Advertisement 2000*.

LSI Solutions®, Sew-Right® SR 5, Advertisement received at ASBS Conference 2002.

Sew-Right® SR 5™ & SR 10™, Ti-Knot® TK 5™ Advertisement received at ASBS Conference 2002.

Three-dimensional manometric imaging of the lower esophageal sphincter, Hubert J. Stein, Md. *Surgery*, 1995 vol. 117 No. 6 pp. 692-698.

A new method of enteroscopy—The double-balloon method, Yamamoto et al., *Can J. Gastroenterol*, vol. 17, No. 4 Apr. 2003, pp. 273-274.

Radiocontrolled Movement of a Robot Endoscope in the Human Gastrointestinal Tract, Paul Swain et al., Abstract—*Gastrointestinal Endoscopy*, vol. 61, No. 5 DDW Abstract Issue: Apr. 2005.

Techniques for Advancing Guide Wires and Devices in the Lumen of the Gastrointestinal Tract, Long et al., *Gastrointestial Endoscopy*, vol. 57, No. 5 Apr. 2003 Abstract, 2003 ASGE Meeting, May 18-21, Orlando Florida.

International Search Report for PCT/US07/09956 mailed Dec. 28, 2007.

Notice of Allowance, U.S. Appl. No. 11/400,724 mailed Sep. 20, 2010 in 7 pages.

Notice of Allowance, U.S. Appl. No. 11/430,677 mailed Sep. 23, 2010 in 7 pages.

Notice of Allowance, U.S. Appl. No. 11/430,274 mailed Sep. 30, 2010 in 8 pages.

Fobi, M.D., Mathais A.L. et al., "Gastric Bypass Operation for Obesity", World J. Surg., Sep. 1998, vol. 22, pp. 925-935.

Pories, M.D., Walter J. et al., "Who Would Have Thought It? An Operation Proves to Be the Most Effective Therapy for Adult-Onset Diabetes Mellitus", Annals of Surgery, Sep. 1995, vol. 222, No. 3, pp. 339-352.

Sugerman, M.D., Harvey J. et al., "Weight Loss With Vertical Banded Gastroplasty and Roux-Y Gastric Bypass for Morbid Obesity With Selective Versus Random Assignment", The American Journal of Surgery, Jan. 1989, vol. 157, pp. 93-102.

Keyser, M.D., Eric J. et al., "Double Closed Loop Obstruction and Perforation in a Previous Roux-en-Y Gastric Bypass", Obesity Surgery, 1998, vol. 8, pp. 475-479.

Oh, M.D., Chung H. et al., "Weight Loss Following Transected Gastric Bypass with Proximal Roux-en-Y", Obesity Surgery, 1997, vol. 7, pp. 142-147.

Crampton, MBBS, Nicholas A., et al., "Silastic Ring Gastric Bypass: Results in 64 Patients", Obesity Surgery, 1997, vol. 7, pp. 489-493.

\* cited by examiner

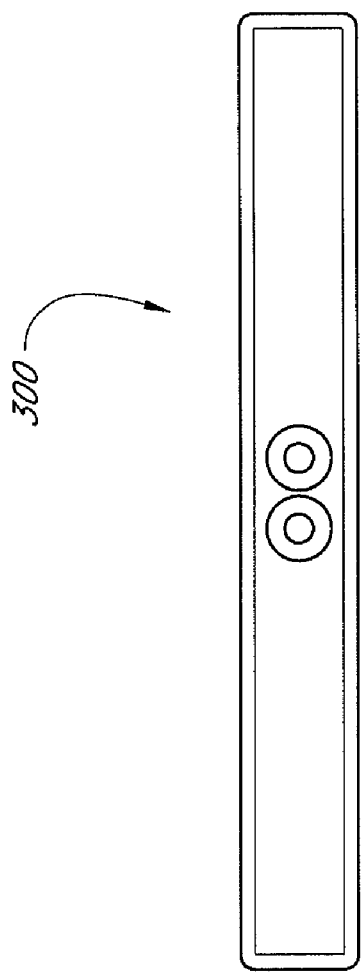
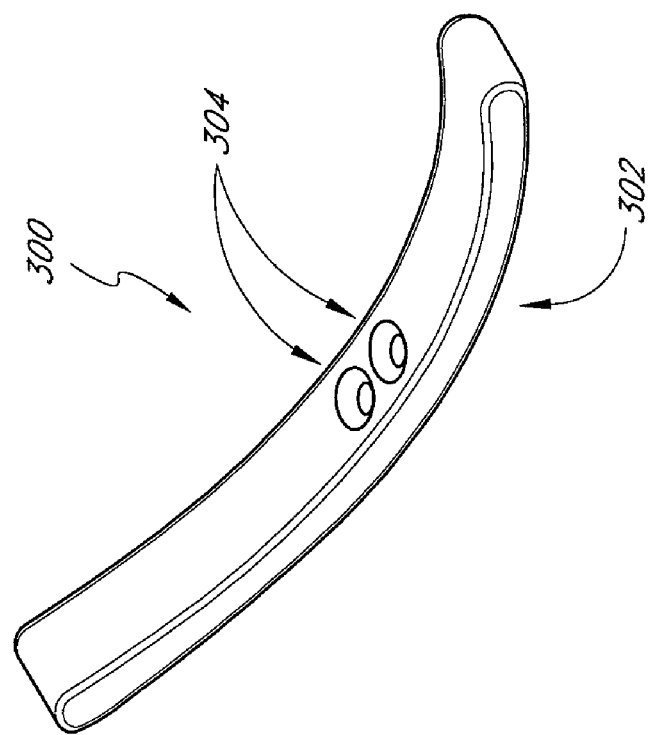
FIG. 14B
FIG. 14A

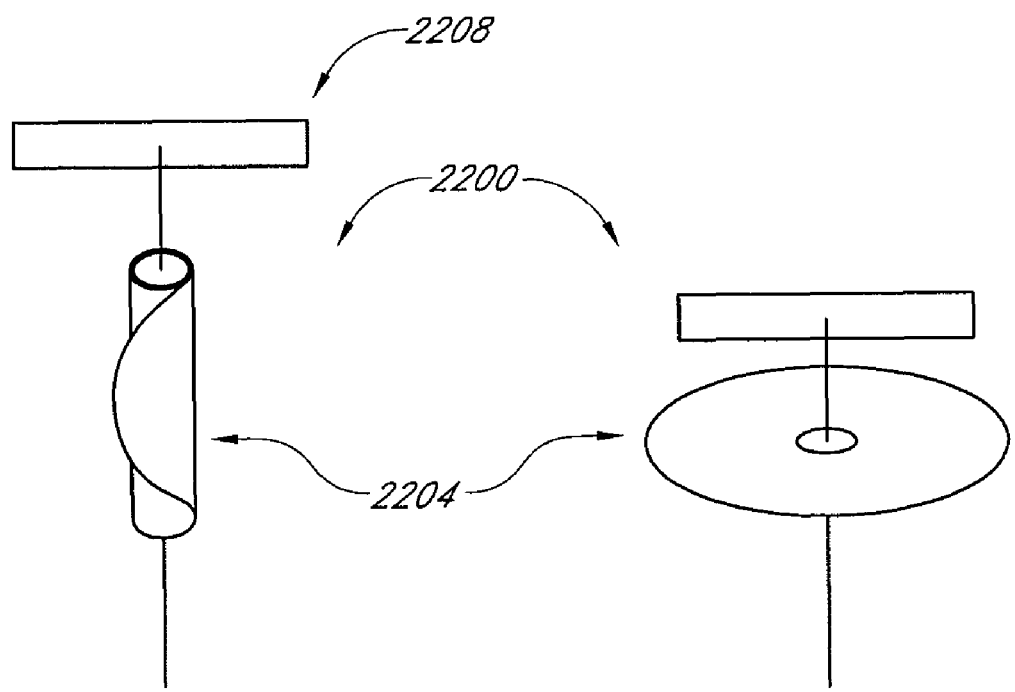
*FIG. 15A*  *FIG. 15B*
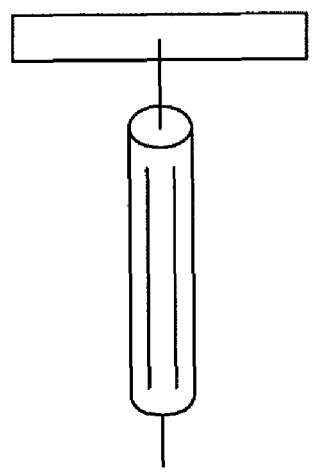  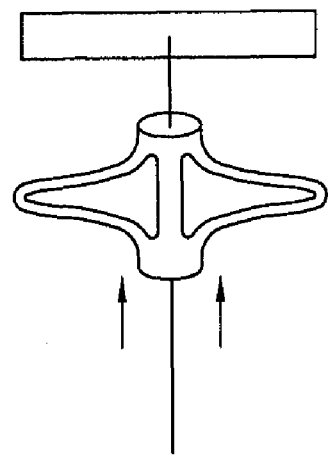
*FIG. 16A*  *FIG. 16B*

METHODS AND DEVICES FOR GASTROINTESTINAL STIMULATION

CROSS-REFERENCE TO RELATED APPLICATIONS

The present application claims priority under 35 U.S.C. §119(e) to U.S. Provisional Application No. 60/794,772, filed Apr. 25, 2006 which is herein expressly incorporated by reference in its entirety.

BACKGROUND OF THE INVENTION

1. Field of the Invention

The invention relates generally to stimulation of the gastrointestinal tract with implanted electrodes.

2. Description of the Related Art

Gastrointestinal sleeve devices for treatment of obesity have been described in prior applications, as have various devices and methods for attachment of a gastrointestinal sleeve device within a patient's digestive tract. The present invention is directed to methods and devices for implantation of at least one electrode within the gastrointestinal tract, to deliver electrical stimulation.

SUMMARY OF THE INVENTION

In one embodiment of the invention, disclosed herein is a gastrointestinal stimulation system, that includes a gastrointestinal bypass sleeve and an electrical stimulator component. In some embodiments, the electrical stimulator component is attached to the sleeve. The system can also include a gastrointestinal attachment cuff having a tubular body, a proximal end and a distal end. The electrical stimulator component can include a circuit board and a battery; a conductive element; and at least one electrode.

In some embodiments, the stimulator component includes at least about two, three, four, five, or more electrodes. A first and a second electrode can be spaced at least about 1 cm, 2 cm, 3 cm, 4 cm, 5 cm, 10 cm, 15 cm, 20 cm, or more apart in some embodiments. In other embodiments, a first and a second electrode can be spaced apart between about 1-20 cm, 2-10 cm, 3-8 cm, or 3-5 cm. In some embodiments, the battery is configured to be recharged using RF energy.

The conductive element can be a ribbon. The ribbon can have a U-shaped, S-shaped, or linear cross-section. The circuit board and battery can be hermetically sealed in a base housing. The base housing can be attached to the outer diameter of the sleeve, or the inner diameter of the sleeve. The electrical stimulator can be triggered by a sensor configured to detect pressure, temperature, pH, motion, and/or strain. The electrode can be annular band-shaped. In some embodiments, the conductive element is a lead wire. In some embodiments, the system includes at least one biasing element operably connected to an electrode. The biasing element can be configured to increase one of the contact surface area or the contact surface time between the electrode and a lumen of the gastrointestinal tract. In some embodiments, the biasing element is configured to increase the contact surface area between the electrode and a lumen of the gastrointestinal tract. In some embodiments, the biasing element is a continuous helical band. In other embodiments, the biasing element is a ring. Alternatively, the biasing element can be a flexible tube, and the electrode is positioned on an outer surface of the tube. In some embodiments, the gastrointestinal bypass sleeve is at least partially inverted within itself, and adapted for eversion within the gastrointestinal tract.

Also disclosed herein is a gastrointestinal stimulation system that includes a electrical stimulator component, the stimulator component comprising a circuit board and a power source contained within a base housing; a conductive element; and at least one electrode; wherein the stimulator component is configured to be transmurally attached with a plurality of tissue anchors to a wall of the gastrointestinal tract.

Also disclosed herein is a method of treating a patient, including the steps of providing an electrical stimulator component, the stimulator component comprising a circuit board and a power source contained within a base housing; a conductive element; and at least one electrode; positioning the base housing of the electrical stimulator component in the patient's digestive tract such that the base housing is positioned in the vicinity of the gastroesophageal junction; securing the base housing to a structure in the vicinity of the gastroesophageal junction, positioning the electrode within the intestine such that the electrode contacts the wall of the intestinal lumen; and stimulating the intestinal lumen. The securing step can include advancing at least one, two, three, four, or more tissue anchors through the tissue wall and positioning a retention surface on each tissue anchor in contact with the serosal surface.

Also disclosed herein is a method of treating a patient, including the steps of providing a gastrointestinal sleeve device having an elongate tubular body, with a proximal end and a distal end; providing an electrical stimulation component comprising: a circuit board and a battery contained within a base housing; a conduction element; and at least one electrode operably attached to the sleeve device; positioning the gastrointestinal sleeve device in the patient's digestive tract such that the proximal end of the tubular body is positioned in the vicinity of the gastroesophageal junction to receive ingested material from the patient's esophagus and the distal end of the tubular body is positioned in the patient's intestine; positioning the base housing in the vicinity of the gastroesophageal junction; securing the proximal end of the sleeve device and the base housing of the electrical stimulator component in the vicinity of the gastroesophageal junction; securing the base housing of the sleeve device in the vicinity of the gastroesophageal junction, and everting the sleeve to position the distal end and the electrode within the intestine.

In addition, disclosed is a method of treating a patient, including the steps of providing a gastrointestinal sleeve device having an elongate tubular body, with a proximal end and a distal end; providing an electrical stimulation component comprising: a circuit board and a battery contained within a base housing; a conduction element; and at least one electrode; positioning the gastrointestinal sleeve device in the patient's digestive tract; positioning the base housing in the patient's gastrointestinal tract; and treating a patient using both the bypass sleeve and the electrical stimulator device. The base housing can be operably attached to the sleeve. In some embodiments, positioning of the electrical stimulation device and the gastrointestinal sleeve device does not occur during the same procedure. The method can also include the steps of providing a gastric space-filling device operably attached to the base housing of the electrical stimulation component; and deploying the space-filling device within the stomach. In some embodiments, the space-filling device is a balloon, solid implant, or a bezoar.

BRIEF DESCRIPTION OF THE FIGURES

FIGS. 13E-19D illustrate attachment mechanisms, including T-tags and T-pledgets that can be used for a gastrointestinal stimulation system, according to some embodiments of the invention.

DETAILED DESCRIPTION OF THE PREFERRED EMBODIMENT

Figure 1:
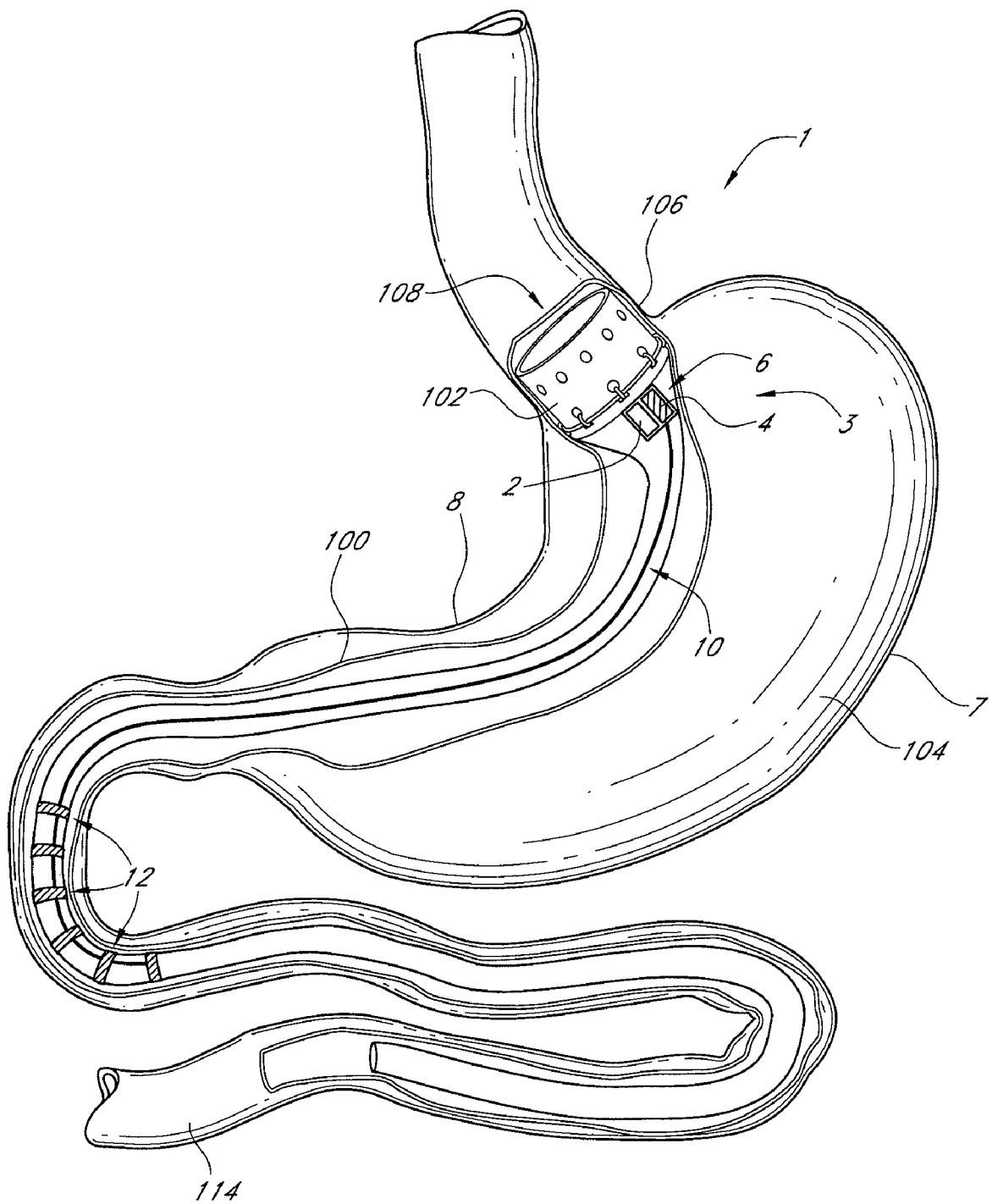
FIG. 1 schematically illustrates one embodiment of a gastrointestinal stimulation system that includes a cuff, sleeve, and electrical stimulation component including a plurality of annular band electrodes.

The present invention provides methods and devices for implantation of at least one electrode within a body lumen, which may be the gastrointestinal tract, to deliver electrical stimulation. The electrodes may be supported by an endolumenal bypass sleeve, or by an attachment cuff, as have been described in U.S. patent application Ser. No. 10/698,148, filed Oct. 31, 2003, published May 13, 2004 as U.S. Patent Pub. No. 2004-0092892 A1 and entitled "APPARATUS AND METHODS FOR TREATMENT OF MORBID OBESITY" (and may be referred to herein as the "Kagan '148 Application"); U.S. patent application Ser. No. 11/025,364, filed Dec. 29, 2004, published Aug. 11, 2005 as U.S. Patent Pub. No. 2005-0177181 A1 and entitled "DEVICES AND METHODS FOR TREATING MORBID OBESITY" (and may be referred to herein as the "Kagan '181 Application"); U.S. patent application Ser. No. 11/124,634, filed May 05, 2005, published Jan. 26, 2006 as U.S. Patent Pub. No. 2006-0020247 A1 and entitled "DEVICES AND METHODS FOR ATTACHMENT OF AN ENDOLUMENAL GASTROINTESTINAL IMPLANT" (and may be referred to herein as the "Kagan '634 Application"); U.S. patent application Ser. No. 11/400,724, filed Apr. 7, 2006, published Jan. 11, 2007 as U.S. Patent Pub. No. 2007-0010794 A1 and entitled "DEVICES AND METHODS FOR ENDOLUMENAL GASTROINTESTINAL BYPASS" (and may be referred to herein as the "Dann '724 Application"); and U.S. patent application Ser. No. 11/548,605, filed Oct. 11, 2006, entitled "DEVICES AND METHODS FOR ENDOLUMENAL GASTROINTESTINAL BYPASS" (and may be referred to herein as the "Dann '605 Application") the disclosures of which are incorporated by reference in their entireties herein. As will be apparent from the descriptions below, in some embodiments, the electrodes may alternatively be attached to nontubular support structures such as an elongate flexible ribbon or tether, which is in turn attached to the wall of the GI system using the transmural anchoring techniques disclosed in the above referenced patent applications. Alternatively, the structure could be held in place via non-transmural devices that resist the natural tendency of the GI tract to expel devices from the system. Examples of suitable non-transmural devices include gastric balloons and bezoars or other devices large enough to resist passage through the pylorus or out through the esophagus once implanted in the stomach. Other devices include stent like structures placed either in the esophagus or the stomach that may hold the stimulator in place through apposition of the structure to the stomach or luminal wall. These devices could also be placed inside or past the pylorus.

Cuff and/or Sleeve System With Stimulation

The method and devices used for attaching a cuff and/or sleeve as disclosed in the aforementioned patent applications could further incorporate an electrical stimulation component as part of the sleeve, or just attached to the cuff in some embodiments. A gastrointestinal (GI) stimulation device, in some embodiments, preferably includes a power source, such as a battery, and is used to deliver energy to any portion of the GI tract, such as a lumen. In some embodiments, the energy is preferably not delivered to the stomach even though the device may be attached in the stomach or the gastro-esophageal junction.

The device is intended to treat obesity, any of the co-morbidities associated with obesity including diabetes; GI inflammatory diseases (e.g., Crohn's disease, ulcerative colitis, celiac sprue), GI hypermotility and well as hypomotility disorders (e.g., gastroparesis, ileus, bowel obstructions, achalasia, irritable bowel syndrome, Hirschprung's disease, toxic megacolon, Ogilvie's syndrome), malabsorptive disorders, and any other disease with manifestations involving the GI tract.

The electrodes would preferably stimulate the lumen distal to the stomach. They could be placed in the pylorus, duodenum, ileum, jejunum, colon or any combination of these sections of the GI tract. In other embodiments, the electrodes could stimulate the lumen of the stomach or esophagus. In still other embodiments, the electrodes could stimulate the lumen of the biliary tree, such as the common bile duct, cystic duct, hepatic duct, or pancreatic duct; or other structures such as the sphincter of Oddi.

Not to be restricted by theory, the stimulation could be used to reduce the feeling of hunger or it could increase or decrease the rate of peristalsis-to increase or decrease the rate at which food passes or it may act to accelerate or inhibit absorption of digested material by increasing or reducing the activity of the active transport mechanisms in the intestinal wall.

Triggering

The stimulator could operate on a constant program, variable program, or a sensor that detects the intake of food and/or liquid could trigger a stimulation program. If it is triggered by a sensor detecting intake of foods and/or liquid it could be preset to run for a specific period of time following that triggering mechanism.

Variables that could be detected by the sensor include pressure, temperature, motion, strain or pH to indicate the intake of food or liquid.

Stimulator Device Description

In one preferred embodiment, the electrical stimulator would include a power source, a circuit board, a conductive element, and at least one electrode configured to transmit the energy to the lumen. The power source is most preferably a battery. The circuit board is most preferably a printed circuit board, although wire-wrapped or point-to-point constructed circuits could also be used. The battery and printed circuit board could be, in some embodiments, part of the cuff or part of the sleeve. If the battery and circuit board are part of the sleeve, they could be near the intake end of the sleeve or alternatively could be placed at a distance from the intake end, such as past the pylorus, to help reduce any direct weight on the anchor points or cuff/sleeve attachment.

The circuit board and power source are most preferably hermetically sealed together in an electrical stimulator base housing. One way to seal the housing of the device would be to encase it in a metal foil. The printed circuit board would preferably generate an oscillating circuit that would be used to drive the stimulator. The voltage, pulsewidth, frequency and duty cycle can be programmable, or they could be pre-programmed before implantation.

In some embodiments, the electrical stimulator preferably has a preset operating frequency and period which can vary according to the alteration of stomach motility to be obtained and/or to the pathological condition of the patient. Generally, the electrical stimulator has an operating frequency of about 2 to about 30 pulses per minute. Preferably, the process of this invention employs stimulation of the small intestines at a rate of about 2 to about 30 pulses/minute with each pulse lasting about 0.1 to about 4 seconds such that there is a pause of about 3 to about 30 seconds between the pulses. The electrical discharge of each pulse can vary from approximately 1 to 15 volts for voltage-controlled stimulation and from 2 to 15 milliamperes for constant current stimulation. More preferably, the pulse rate is about 12 to about 14 pulses/minute with each pulse lasting about 0.1 to about 0.5 seconds with a pause of about 4.5 to about 5 seconds between pulses. Preferably, the pulse amplitude is about 0.5 to about 15 milliamps. More preferable, each pulse consists of a train of micro-bursts with a frequency of about 5 to about 100 Hz.

The stimulator base housing would preferably be placed on the outside diameter of the sleeve so it would not interfere with food passing through the sleeve, however it could also be sealed between layers of the sleeve material. This may help further protect the stimulator from any exposure to stomach acid or other material.

FIG. 1 illustrates a gastrointestinal stimulation system 1 that includes a gastrointestinal sleeve device 100 attached to an artificial attachment cuff or stoma device 102 implanted within a patient's stomach 104. The attachment cuff 102 can be implanted in the vicinity of the gastroesophageal junction 106, or at the outlet of a surgically created gastric pouch (not illustrated). The attachment cuff 102 preferably does not restrict the flow of food, although it may be provided with a restrictive opening if desired. The cuff 102 can have a fixed diameter opening 108 equal to, larger or smaller than the fully open diameter at the native GEJ. Alternatively, the cuff 102 can have an adjustable stoma opening or it can be a "smart" stoma that adjusts the size of the stoma opening in response to various conditions.

The attachment cuff 102 is preferably configured for per-oral delivery and attachment using endoscopic techniques. Alternatively, the cuff 102 can be implanted using laparoscopic or open surgical techniques. Additional details of the cuff, stoma and attachment can be found, for example, in any of the related applications incorporated by reference herein, such as, for example, the Dann '605 application.

The stimulation system 1 shown in FIG. 1 also includes an electrical stimulation component 3 including a battery 2 and circuit board 4 preferably hermetically sealed within in a base housing 6. As illustrated, the base of the stimulation component 6 is shown closer to the greater curve 7 of the stomach 104. The base housing 6 of the device 3 may be placed at any location on the circumference of the sleeve 100 and there may be advantages to being placed on the lesser curve 8 side of the circumference, or any other aspect of the sleeve 100. In addition the stimulator base 6 could be attached to the sleeve at some distance farther away from the cuff 102 than depicted in the drawing, e.g., at least about 25 cm, 50 cm, 75 cm, 100 cm, 125 cm, or more.

The electrical stimulation component 3 preferably also includes a conductive element 10, which can be a lead wire in some embodiments, and that, as depicted in FIG. 1, could be a bundle of multiple wires to individually power one or more electrodes 12. Alternatively, there could be more than one electrode 12 per wire 10. The optimal configuration would be driven by the desired stimulation program. The electrodes 12 shown in FIG. 1 can be in the shape of an annular band that can partially or fully circumscribe a portion of the sleeve 100. However, various other sized and shaped electrodes are contemplated as well. Alternatively, the electrodes could be connected wirelessly to the stimulator. One of ordinary skill in the art would be able to select an appropriate method for wireless stimulation of an electrode, such as, for example, as described in U.S. Patent Publication No. 2006-0085042 to Hastings et al., hereby incorporated by reference in its entirety. This technology could be advantageous because it could allow a stimulator to be placed in traditional surgical implantation techniques or worn external to the body while the electrodes reside in the lumen of the GI tract.

The battery 2 for the stimulation component 3 could be relatively small, as the sleeve 100 is not necessarily designed as a permanent implant, although permanent implants are also contemplated. One example of a stimulation component's specified energy and lifespan of the device with a battery is described below.

Battery/Power Example:

The formula to calculate the energy delivered during a stimulation cycle is:

$$Energy = (Voltage^2/Resistance) * Pulsewidth * Frequency\ of\ Stimulation * Duty\ Cycle$$

Given sample parameters of one embodiment:

Voltage=5 Volts; Resistance=350 Ohms; Pulsewidth=200 microseconds; Frequency=40 Hz; Duty Cycle=40% (2 sec. on and 3 sec. off), the energy delivered for one cycle would be 228 microwatts. Using the formula to determine current:

$$I(current) = Power/Voltage = 228\ microwatts/5\ Volts = 45\ micro\ amps$$

In one embodiment, if a 90 milliampere battery 2 is selected for use for the stimulation element 3, then the lifetime of that battery 2 would be equal $2 \times 10^6$ seconds, or about 23 days. If a longer battery life is desired, a 135 milliampere battery would advantageously increase the battery lifetime by 50%. Batteries in this size would be approximately of that found in watches or calculators.

Electrodes

The electrode(s) 12 of a stimulation component 3 would most preferably contact the inside wall of the lumen. This means some exposed part of the electrode 12 would need to be on the outside surface of the sleeve 100 or if there is no sleeve 100 exposed to the inner surface of the mucosal lining of the lumen. Contact with the lumen can be achieved with a variety of means. In a preferred embodiment, barbs or other forms of fixed attachment to the intestinal wall are not used as this could provide the intestines with a point to pull on the device 3 and cause complications such as an accordion-like response in the intestine, potentially resulting in intussception or volvulus, rupture of the intestinal wall, or detachment of the device's anchor mechanisms. Other embodiments disclosed herein illustrate various different non-limiting electrode shapes and configurations.

The electrodes 12 will typically have sufficient contact with the luminal wall because of the natural tendency for the lumen to close down on whatever is in it. In some embodiments, there could be various biasing elements 16 incorporated into the sleeve that help bias the electrode 12 in a direction to improve the surface area and/or duration of contact. The shape of the electrodes 12 themselves could help induce better contact with the mucosal lining. The electrodes 12 could be a raised form such as pyramid, hemisphere or mushroom shaped to help create better contact. While the electrodes 12 can be placed in contact with the luminal surface, in some embodiments one or more electrodes 12 can be placed on the serosal surface, or even some electrodes 12 in contact with the luminal surface while other electrodes 12 are in contact with the serosal surface.

A stimulation system can involve any number of electrodes 12 depending on the desired clinical result. In some embodiments, a stimulation system has at least about 1, 2, 3, 4, 5, 10, 15, 20, or more electrodes 12. Furthermore, the electrodes 12 can also be spaced apart any appropriate distance depending on the desired clinical result. In some embodiments, a first electrode may be spaced apart from a second electrode by between about 1-20 cm, preferably between about 2-10 cm, in some embodiments between about 3-8 cm, in other embodiments between about 3-5 cm.

Figure 2:
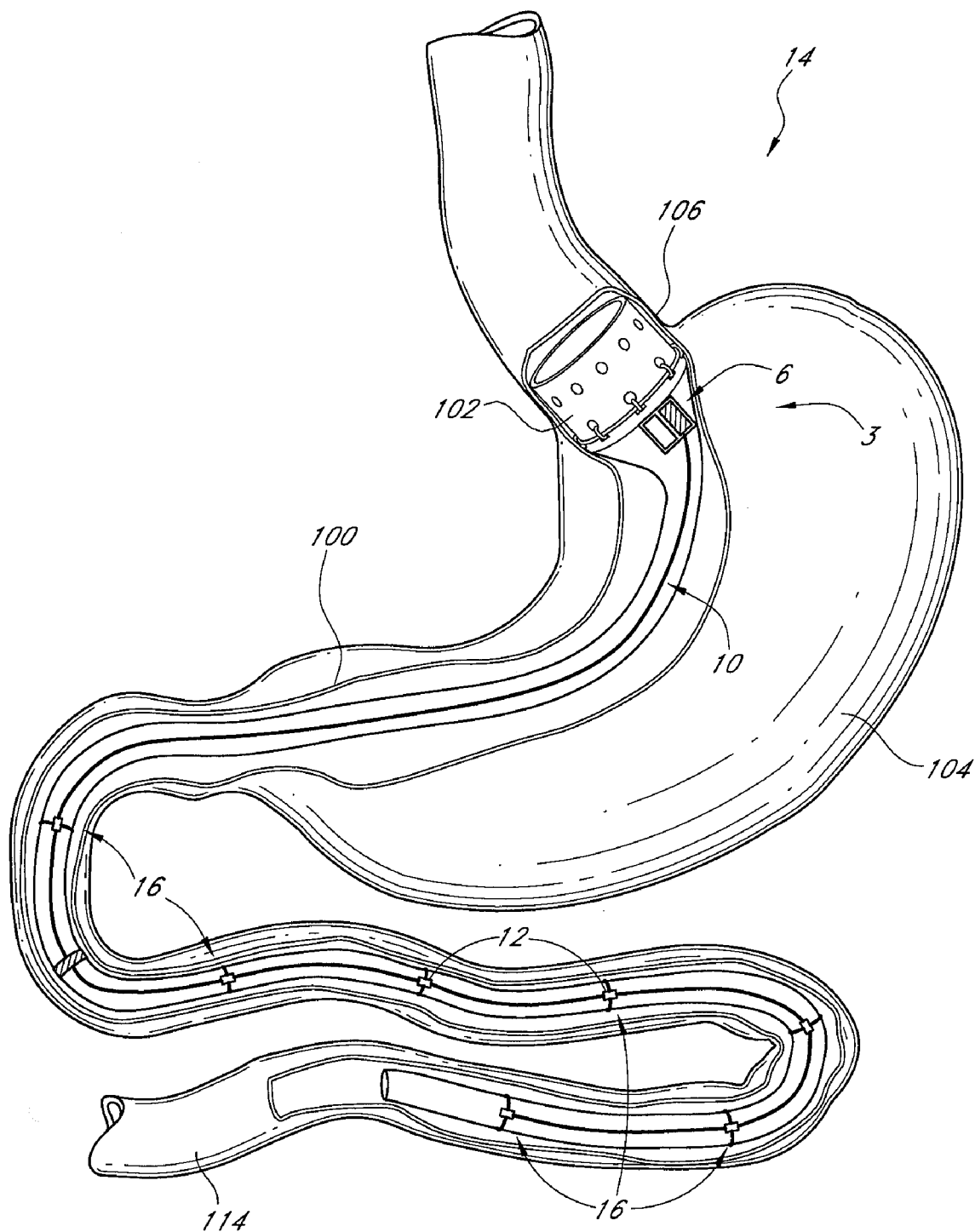
FIG. 2 schematically illustrates an embodiment of a gastrointestinal stimulation system that includes biasing elements in the form of rings, to increase contact surface area and/or time of electrodes to the intestinal lumen.

FIG. 2 illustrates a gastrointestinal stimulation system 14 similar to that of FIG. 1, and including one or more biasing elements 16. The biasing elements 16 as shown schematically in FIG. 2 is a series of one or more rings 16 biased towards an expanded state that are connected by a wire 10 to power the electrodes 12 that are on the rings 16. There could be one or more electrodes 12 on each ring 16. Using rings 16 as biasing elements 16 would be preferable when there is the desire to place multiple electrodes 12 at one circumferential area of the intestine 114.

Figure 3:
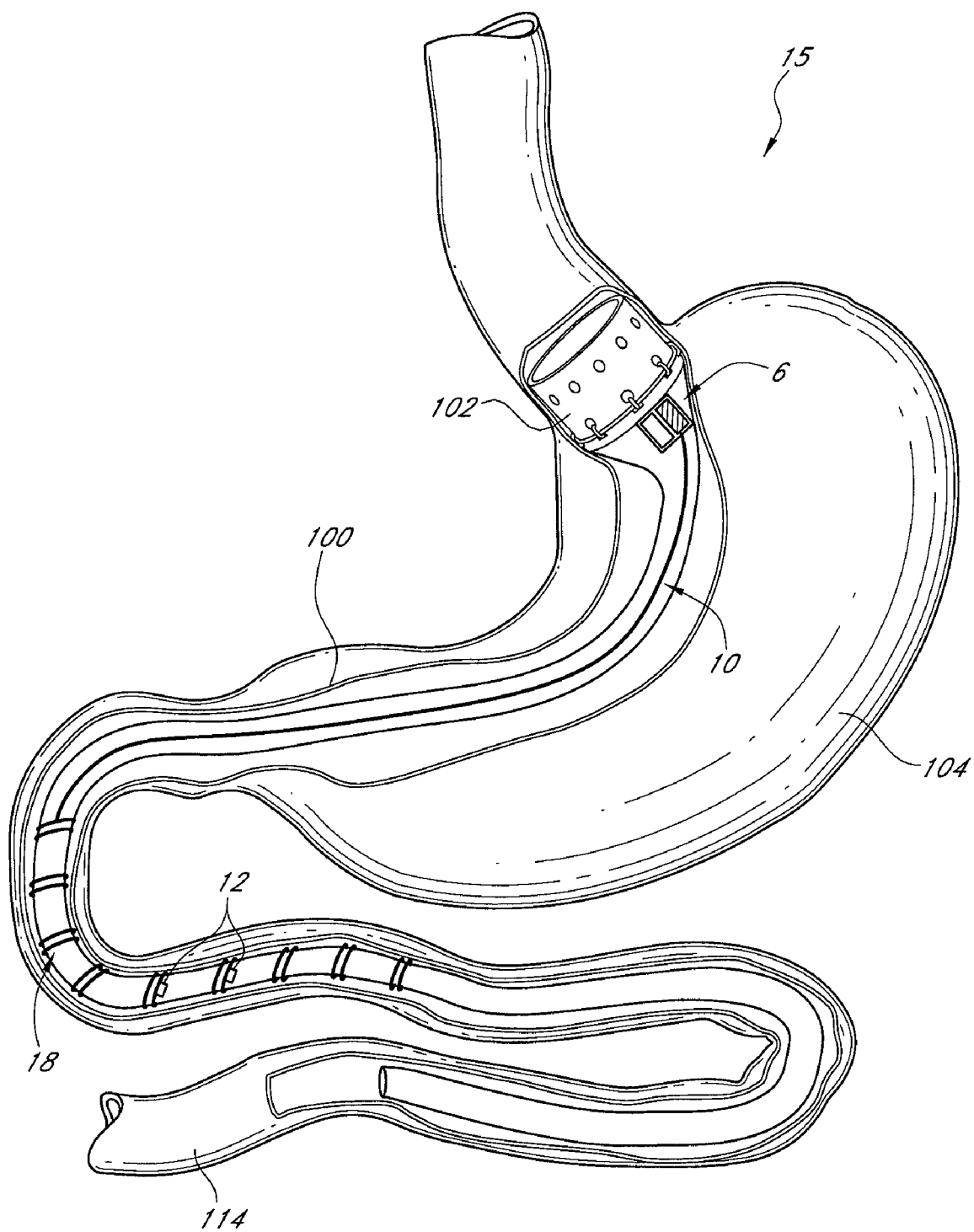
FIG. 3 schematically illustrates an embodiment of a gastrointestinal stimulation system that includes biasing elements in the form of a helical band, to increase contact surface area and/or time of electrodes to the intestinal lumen.

FIG. 3 illustrates a gastrointestinal stimulation system 15 where the biasing element is a helical support structure 18 that runs part of or all of the length of the sleeve 100. The one or more electrodes 12 are most preferably attached to the helical support structure 18. One possible advantage of a helical support structure 18 that is biased towards an expanded state is that, unlike with the rings 16 shown in FIG. 2, there would not be a ring or oval shaped device for the peristaltic contraction to 'pull' on, if this is a factor to consider, as it would tend to collapse as necessary when compressed, but still maintain contact with the lumen. In other embodiments, any support structure of the sleeve 100 described in any of the prior applications incorporated by reference, such as the Dann '605 application, could also incorporate electrodes 12 in its design.

In some embodiments, a biasing element 16 could be made, at least in part, of a super elastic metal, such as Nitinol, other shape meory material, or could be made from plastic or could be a combination of both where the core is Nitinol and they are surrounded by or partially surrounded by a plastic. In this case the plastic could also serve as an insulator where desired.

Programming

The electrical stimulation component 3 could be pre-programmed before placement. There could be a separate programmer remote from the stimulator 3 that could control any of the aspects of the stimulation cycle and/or triggering mechanism of the device wirelessly from outside the patient. The stimulator with one preset program could be used initially. Then, after a certain time, a device with a different program could be switched out. This could occur when replacing the sleeve 100 if the stimulator component 3 is integrated with the sleeve 100. When the sleeve 100 is changed the stimulation program may be varied using the length of the sleeve 100 as a variable and what points of contact in the GI tract are expected to exist with the modified length of tubing. For example, the stimulator component 3 may deliver more energy if there is a shorter sleeve 100 and the stimulator component 3 could deliver less energy through each electrode 12 if there is a longer sleeve 100 or any such combination of these variables could be used.

Rechargeable Battery

In some embodiments, the battery 2 could be recharged wirelessly by an external power source that uses RF energy transmitted through the body to recharge the battery 2, such as transcutaneously. In other embodiments, a terminal is present on the cuff 102 that could be accessed trans-orally to recharge the battery through direct conduction. This could be done during routine follow up with a diagnostic endoscopic procedure to inspect the system in place. In yet other embodiments, the battery 2 could be a simple disposable battery that is configured to run out of charge at or near the time of a scheduled sleeve removal or replacement. One of ordinary skill in the art will appreciate that a wide variety of battery 2 types can be selected for use with the disclosed stimulation systems.

Stimulator Separate from Sleeve

Figure 4:
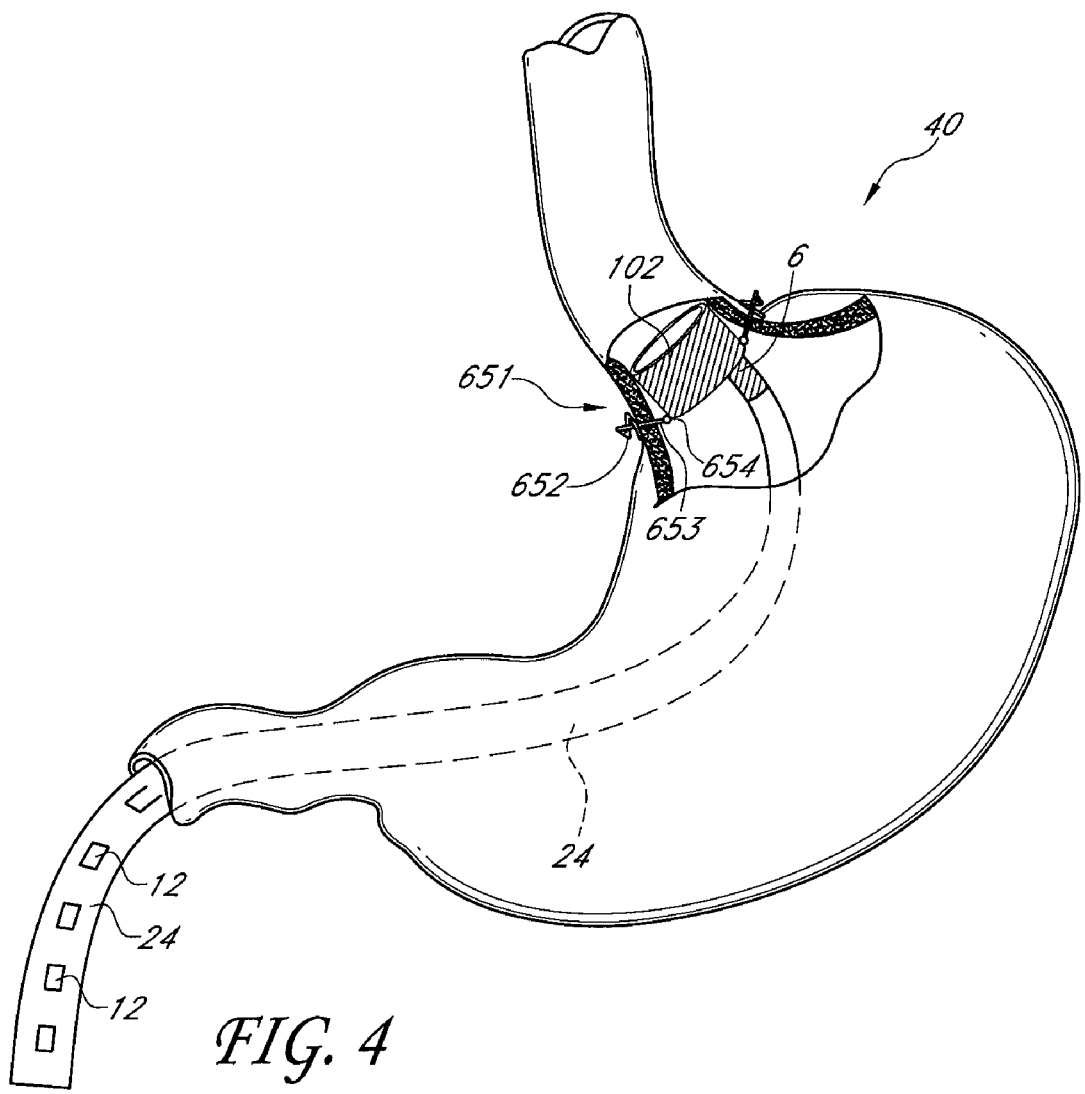
FIG. 4 schematically illustrates an embodiment of a sleeveless gastrointestinal stimulation system.

The stimulator component 3 as described above could also be separate from the sleeve element 100 of the system. In some embodiments, a gastrointestinal stimulation system 40 does not include a sleeve element 100. This would allow for a variety of treatment options. The electrical stimulator base unit 6 could be attached to the cuff 102, such as tethered to the cuff 102, and the electrodes 12 could be on a ribbon 24 or other device that is advanced down the GI tract, as shown in FIG. 4.

Ribbon Type Electrode Connector

The ribbon 24 that holds the electrodes 12 could have a shape that would help bias the electrodes 12 into contact with the lumen. A compliant ribbon 24 may have enough contact with the lumenal wall because of the tendency of the intestine 114 to collapse into a flat configuration.

However, it may be advantageous to have the ribbon 24 take on a predefined shape such as a helix through the use of reinforcement elements in the ribbon 24. In this configuration the electrodes 12 would be oriented to be on the outside of the helical surface of the ribbon 24. These could be stiffer plastic materials or super elastic metals such as Nitinol used to make the helical structure. The ribbon 24 itself may be of a material that could be shape set into this configuration.

Figure 6:
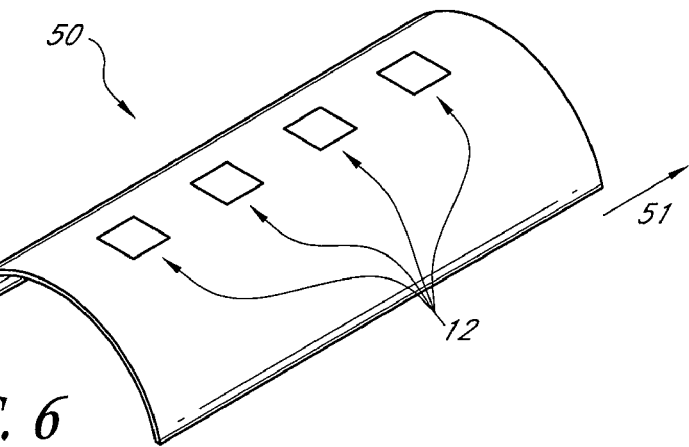
FIGS. 6-8A schematically illustrate cross-sections of various embodiments of ribbon electrodes, according to some embodiments of the invention.
Figure 7:
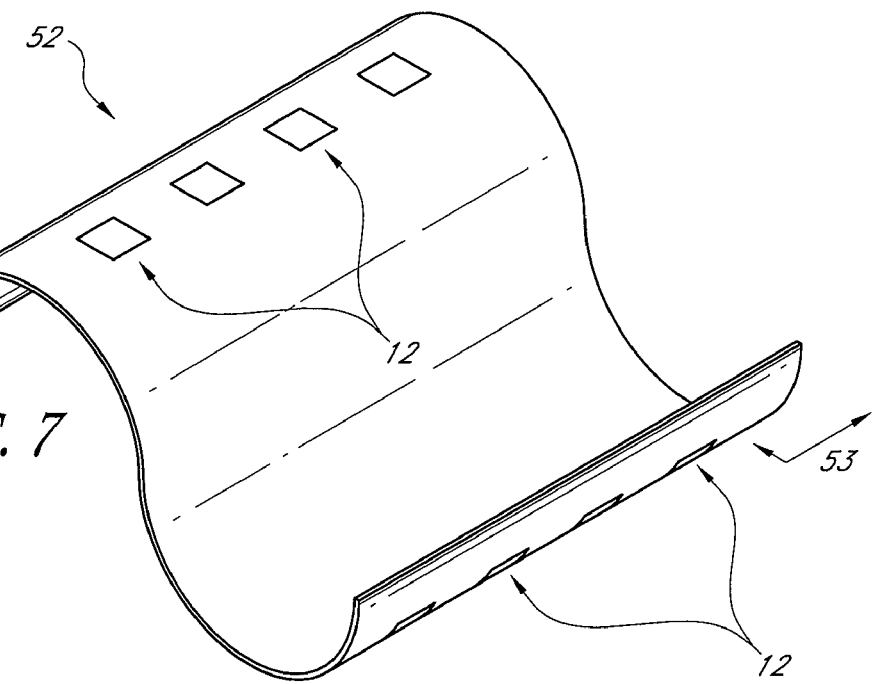
Figure 8:
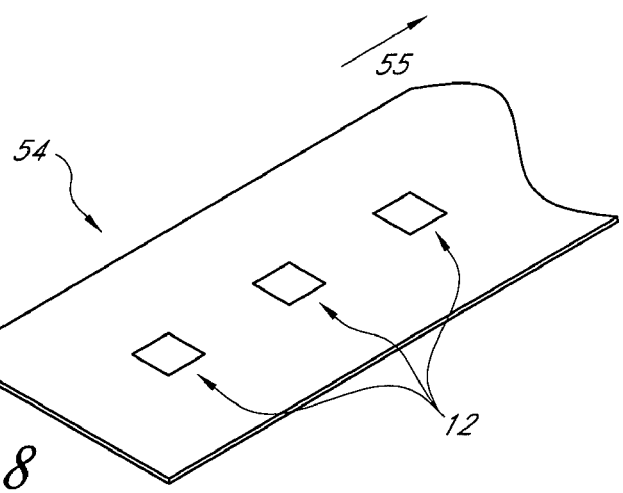

The cross sectional profile of the ribbon 24 could be flat, U-shaped, S-shaped or some other complex form. Some non-limiting embodiments are illustrated in FIGS. 6-8. FIG. 6 illustrates a ribbon 50 with a U shaped cross-section. Ribbons preferably have first and second sides. Electrodes 12 are shown operably attached to the ribbon 50. One end of ribbon connects to the base unit 6 of the stimulation element. FIG. 7 illustrates a ribbon 52 with an S-shaped cross-section. Such an embodiment can have electrodes 12 on both first and second sides of the ribbon 52 as shown. The U shaped 50 or S shaped 52 cross sections as depicted in FIGS. 6-7, advantageously provide elevated areas where electrodes 12 could be placed that may have a higher likelihood of making contact with the lumen. FIG. 8 illustrates an embodiment where the ribbon 54 is substantially flat. Attached to ribbon 54 are electrodes 12 on both the first and second sides of the ribbon 54. In some embodiments, electrodes 12 may be only on either the first or second side of the ribbon 54. Arrows 51, 53, 55, 57 of FIGS. 6-8A, respectively, illustrate a direction in which an end of the ribbon 50, 52, 54 connect to base 6 of stimulator component 3.

Figure 8A:
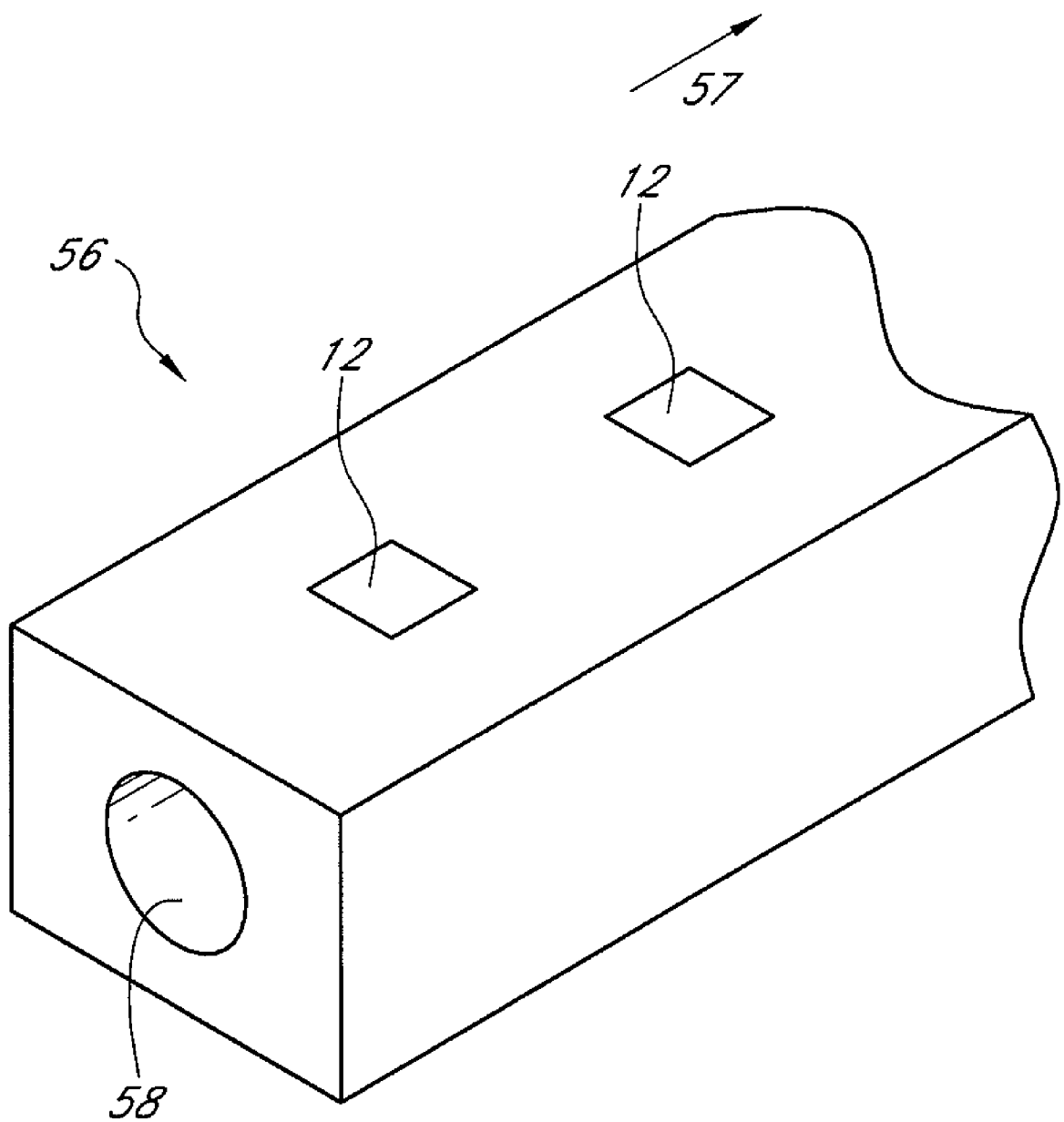

FIG. 8A illustrates a ribbon 56 with operably connected electrodes 12 similar to that shown in FIG. 8A, also having a lumen 58. Lumen 58 is preferably configured to allow a stiffening element (not shown) to pass therethrough in order to provide additional structural support for the ribbon 56. In some embodiments, the stiffening element is a guidewire. The guidewire may have a shape memory material such as Nitinol to allow for possible adjustment should a change in the degree of stiffening be required. Any of the sleeves, such as sleeve 100 disclosed herein can also have one or more lumens (in addition to the artificial stoma for bypass of food contents, etc.) present that are configured to receive a stiffening element.

In some embodiments, the ribbon 24 can have a protrusion, bulge, or balloon (not shown) in its construction on or near the distal end to help transfer a desired amount of force from the peristaltic contractions to help keep the ribbon 24 in place.

Figure 5:
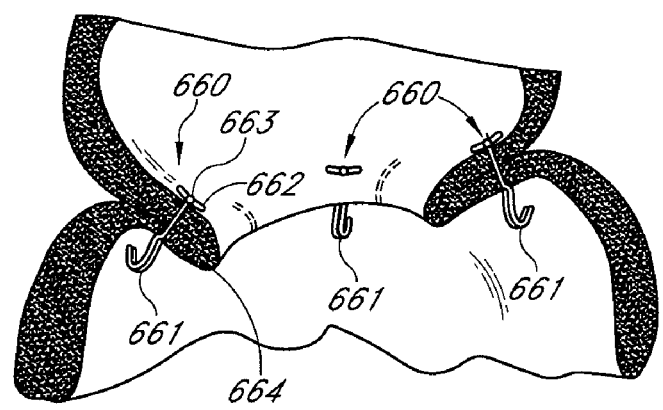
FIG. 5 schematically illustrates an attachment mechanism for a gastrointestinal stimulation system, in one embodiment of the invention.

FIG. 5 shows one embodiment of a fastener 660 comprising a hanger 661 that also functions to hold two layers of folded tissue together. The fastener 660 may be used to secure the base unit 6 of the stimulation component 3 to the mucosal wall. Many other suitable fasteners are disclosed, for example, in the Kagan '634 application. The fastener 660 of FIG. 5 has a toggle 662 that pivots on a hinge 663 so that is can be aligned with the post 664 as it is passed through tissue layers, and can then be pivoted to hold the tissue layers together.

The toggle 662 helps to distribute forces that hold the fastener 660 in place over the length of the toggle 662, and also prevents the fastener 660 from being pulled through the hole. Alternative to the toggle 662, a similar functioning apparatus such as a disc or a multi-arm umbrella could also be used to distribute forces on the adjacent tissues while preventing the fastener 660 from passing through the hole. This fastener functions similarly to the T-tag fasteners described herein. Some of the attachment structures described herein such as that of FIG. 5 are illustrated in connection with tissue plications; however, these attachment structures may also be used transmurally, i.e., through one tissue layer.

Tubular Electrode Connector

In other embodiments, the electrodes 12 could be on the outside of a flexible tube (not shown). The tube could be hollow or solid as desired. The diameter of the tube would be ideally just large enough to allow good contact with the lumen of the intestine but not too large to cause any reaction in the intestine or risk occluding the intestine. If hollow, the ends of the tube would most preferably not be open to keep any food or material from impacting in the tube. A hollow or solid tube could have any of the structural elements as conceived for the sleeve as previously described, for example, spiral reinforcements, ribs, or a larger node near the distal end to help capture force from the peristaltic motion of the intestines. In some embodiments, the tube could have shape set into the tube itself during manufacturing to give it a preferred structure. The tube could form a helical structure to bias an outer surface of the helix into contact with the lumen. The center of the helical structure could be large enough to allow a cuff/sleeve system to be implanted through the center of it. In this way a sleeve could be initially implanted but then removed after a certain period of time and just the stimulator would remain. Alternatively, the stimulator could be removed and the sleeve could remain. In still other embodiments, one of the stimulator or the sleeve could be implanted first and then the other device could be added after a certain period of time These various combinations would allow a wide range of treatment choices based on either how a patient responds to various the different elements of the system or could be used to stage the procedure to build the impact on weight loss. It could also be determined that the sleeve is beneficial for the early resolution of co-morbidities and/or initial weight loss and then after a certain period of time intestinal stimulation is enough to maintain the weight loss.

Stimulator Component Attached Without Cuff or Sleeve.

Figure 9A:
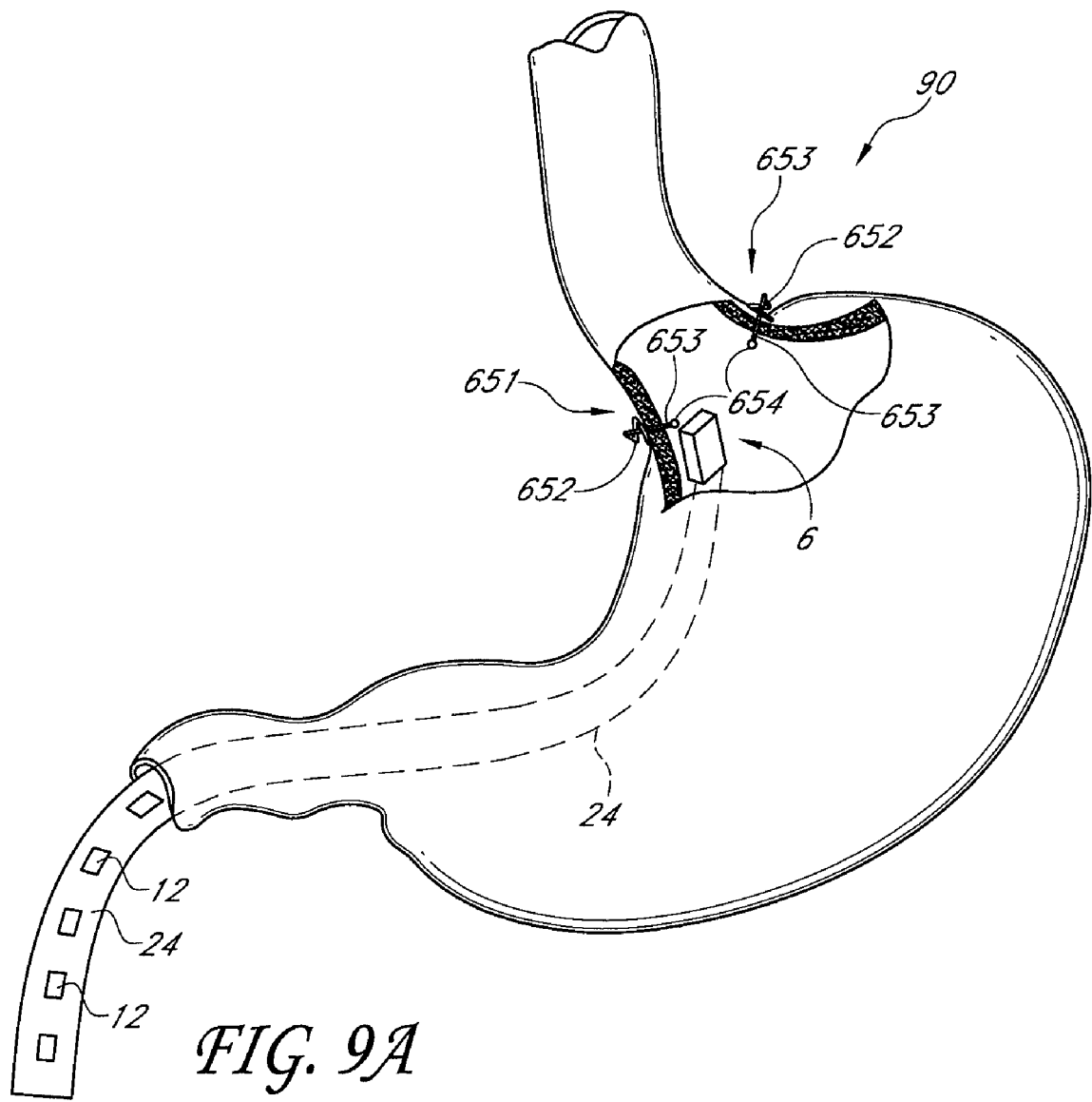
FIG. 9A schematically illustrates a cuff-less, sleeveless gastrointestinal stimulation system where the base stimulator is directly attached to a wall of the GI tract, according to one embodiment of the invention.

In some cases it may be desirable to attach the stimulator to the GEJ without a cuff or sleeve. One such stimulation system 90 is shown in FIG. 9A. In this case the stimulator could be attached directly to a subsection of the GEJ with transmural anchors as described in, for example, the Kagan '634 or Dann '605 applications. As shown in FIG. 9A, in one embodiment, an attachment or fastener device 651 for the base stimulator 6 can be driven through a single tissue layer, with attachment means 654 on the end of a post 653 positioned within the passageway, and a cone shaped spring positioned 652 on the serosal side. The embodiment shown in FIG. 9A is preferably configured so that its installation does not narrow the passageway of the organ. Delivery of fastener embodiments communicating with the exterior of a hollow organ as shown in FIG. 9A may incorporate means to control capture of other structures. Though it may be clinically desirable to capture other structures as in the case of capturing the diaphragm by fasteners placed in the cardia of the stomach it is more likely that this would be undesirable. Fastening means could incorporate shielding means and/or means to invaginate the organ wall as the fastener is advanced through the organ wall.

Also shown in FIG. 9A is a conductive element 24 operably attached to the base stimulator 6 at its proximal end, and having electrodes 12 operably attached to the conductive element 24 within the intestine more distally as shown. In some embodiments as shown, the conductive element 24 can be a ribbon as shown in FIG. 4. In another embodiment, the base stimulator 6 may be attached to the fastener illustrated in FIG. 5.

Figure 9B:
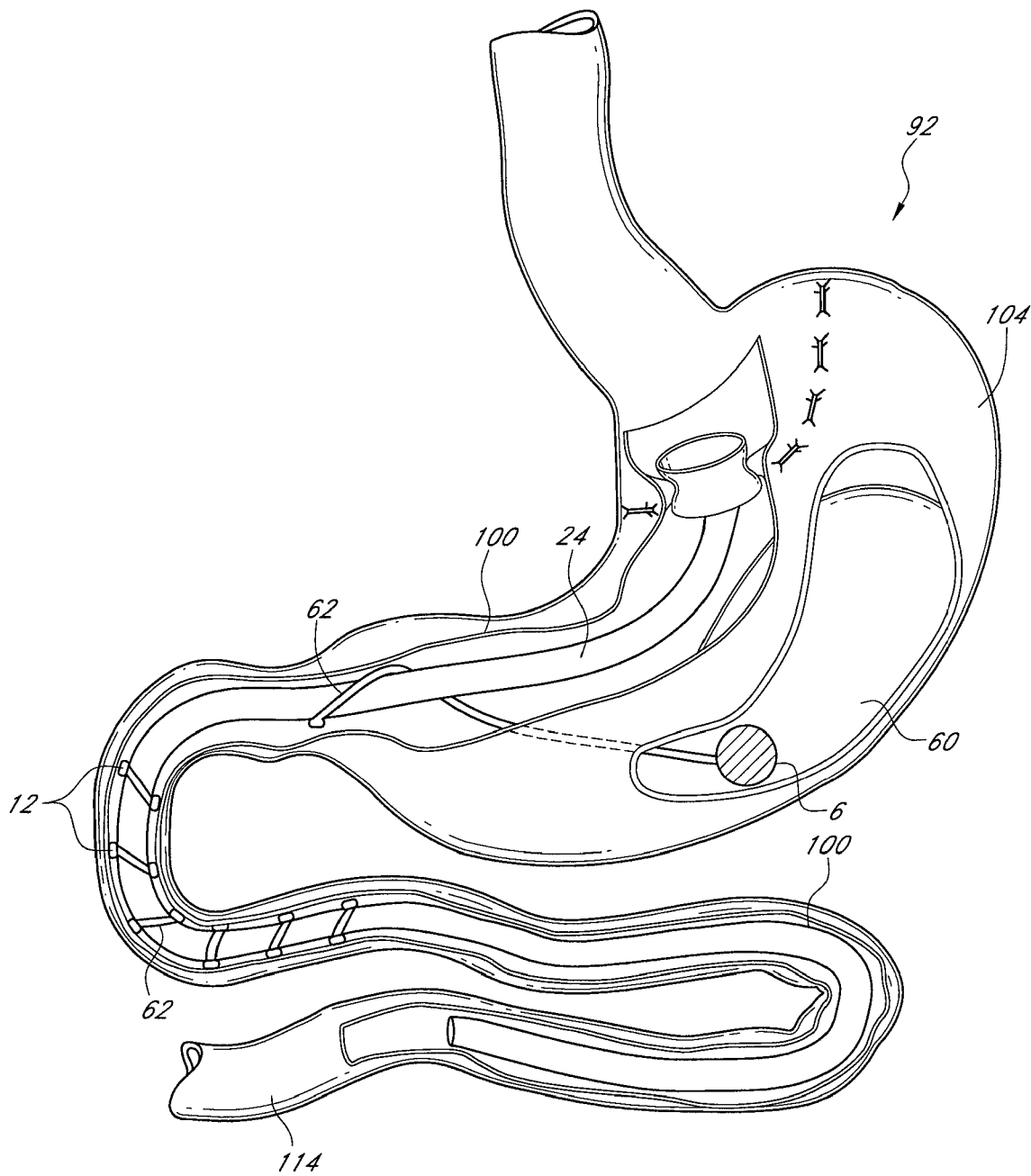
FIG. 9B schematically illustrates a gastrointestinal stimulation system where the base stimulator is attached to a gastric balloon, according to one embodiment of the invention.

Alternatively, as illustrated in the system 92 of FIG. 9B, the base stimulator 6 could be on a device 60 configured to remain in place in the stomach 104 without transmural attachment of device 60 to the stomach 104. Space-occupying devices such as gastric balloons or bezoars are known to those in the art. These are devices that are designed to remain in the stomach after implantation. A stimulator base 6 as described could be attached to such a device 60 or inside the device 60 and the ribbon, tether, or the like holding the electrodes 12 in place would be attached either to the anchoring device 60 and/or the base stimulator 6 itself. In one configuration, there could be a cuff and/or sleeve device (sleeve shown as 12 in FIG. 9B) implanted after a gastric balloon 60 with a base stimulator 6 and conductive element is implanted. In this configuration, there would be a base stimulator 6 as described above and a series of intestinal electrodes 12 with the system not fixedly anchored to tissue. In the embodiment shown, electrodes 12 are preferably raised on top of a helically-biased tube 62 (which may be the conductive element 10, or could alternatively serve as a scaffolding for a lead wire in some embodiments) separate from, but wrapped around the outer diameter of the sleeve 100.

Subsection of the GEJ for Attachment

In some embodiments, a preferred location to attach the base 6 of the stimulator component 3 is selected. For example, the side of the GEJ closest to the lesser curve of the stomach may have characteristics such as lesser motility or a different type of tissue that makes it better to attach the stimulator base 6.

Note that the part of the GEJ closest to the lesser curve of the stomach can be an ideal place to attach other devices in the stomach besides a stimulator. It could be an advantageous anchor point for volume occupying devices or other sensors to monitor physiologic parameters such as pH.

When the stimulator is attached directly to the GEJ without a cuff or sleeve the ribbon type electrode as described above could be used, or any other type of flexible connector for connecting the intestinal electrodes to the stimulator Toposcopic Delivery In some embodiments, a gastrointestinal stimulation system can be placed in a patient using a toposcopic delivery method, such as a method similar to that disclosed in the Dann '605 application. Other useful devices and methods for toposcopic access and delivery are disclosed in U.S. Provisional Patent Application No. 60/826,862 to Dann et al., filed on Sep. 25, 2006 and hereby incorporated by reference in its entirety. Embodiments of gastrointestinal stimulation systems that are configured to be delivered toposcopically most preferably include electrodes operably attached to sleeve elements, such as, for example, the embodiments illustrated in FIGS. 2 and 3. However, toposcopic delivery of other embodiments, such as wireless electrodes, is also possible.

Figure 10A:
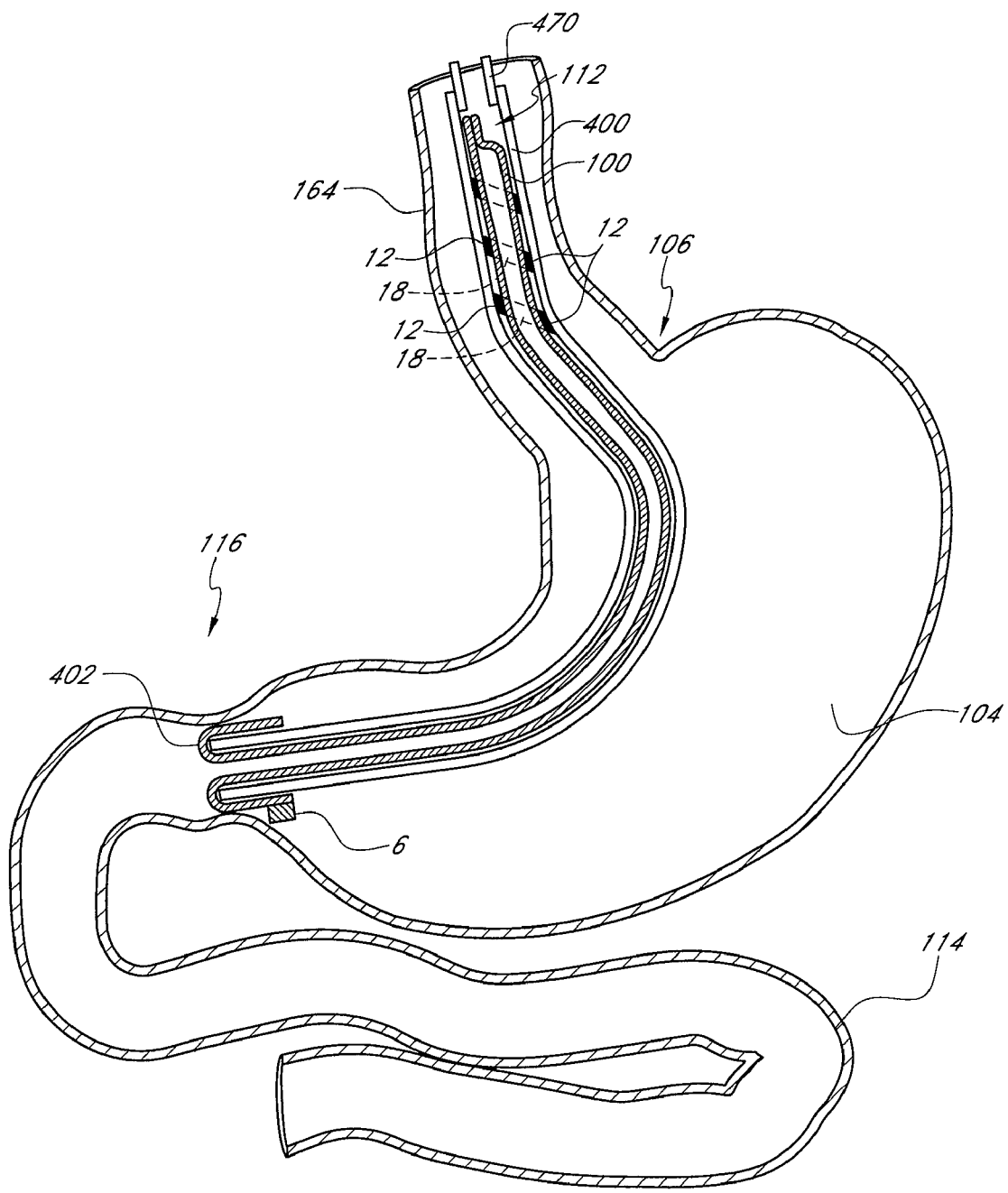
FIGS. 10A-C schematically illustrate steps showing toposcopic delivery of a gastrointestinal stimulation system, according to one embodiment of the invention.
Figure 10B:
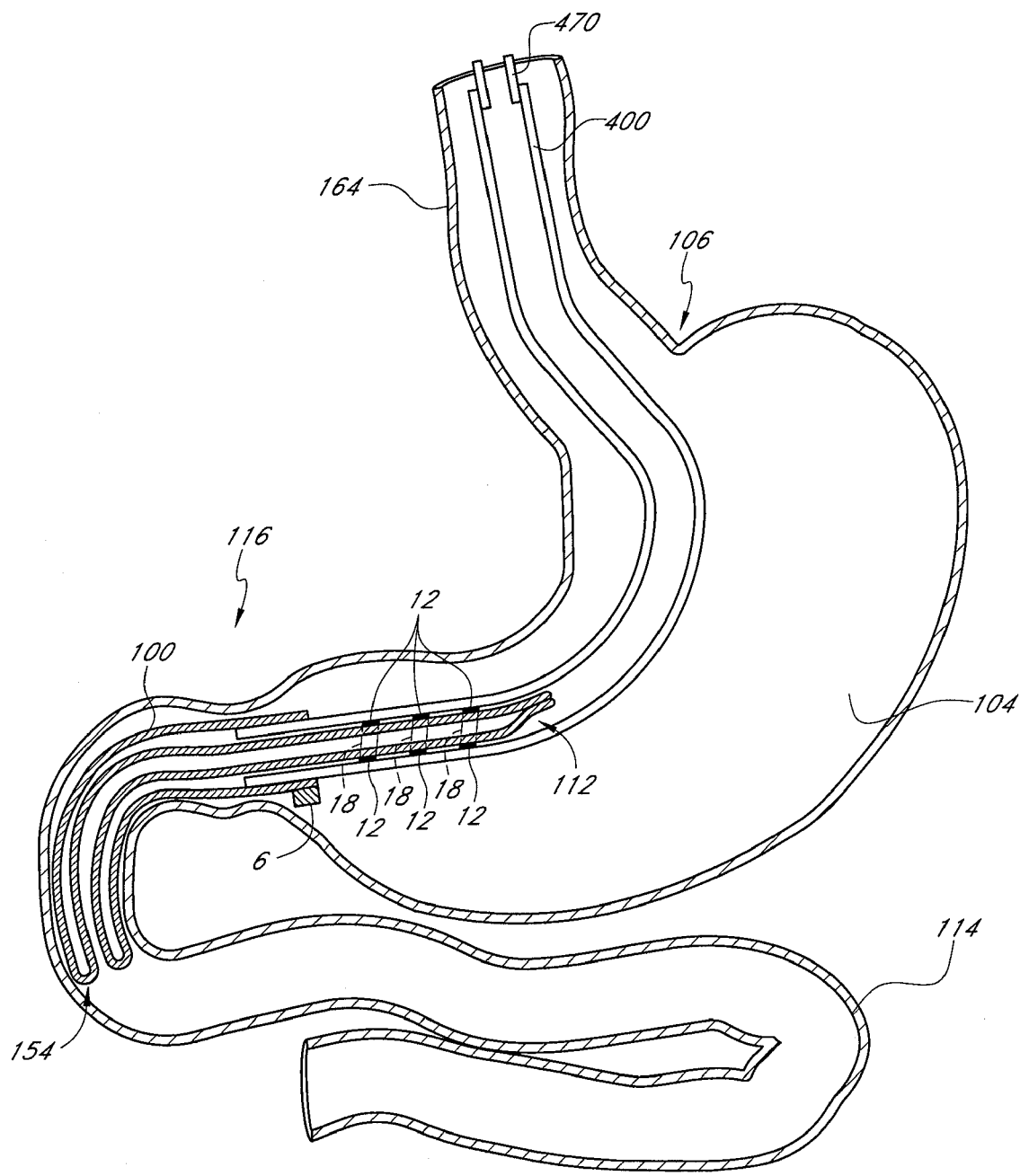
Figure 10C:
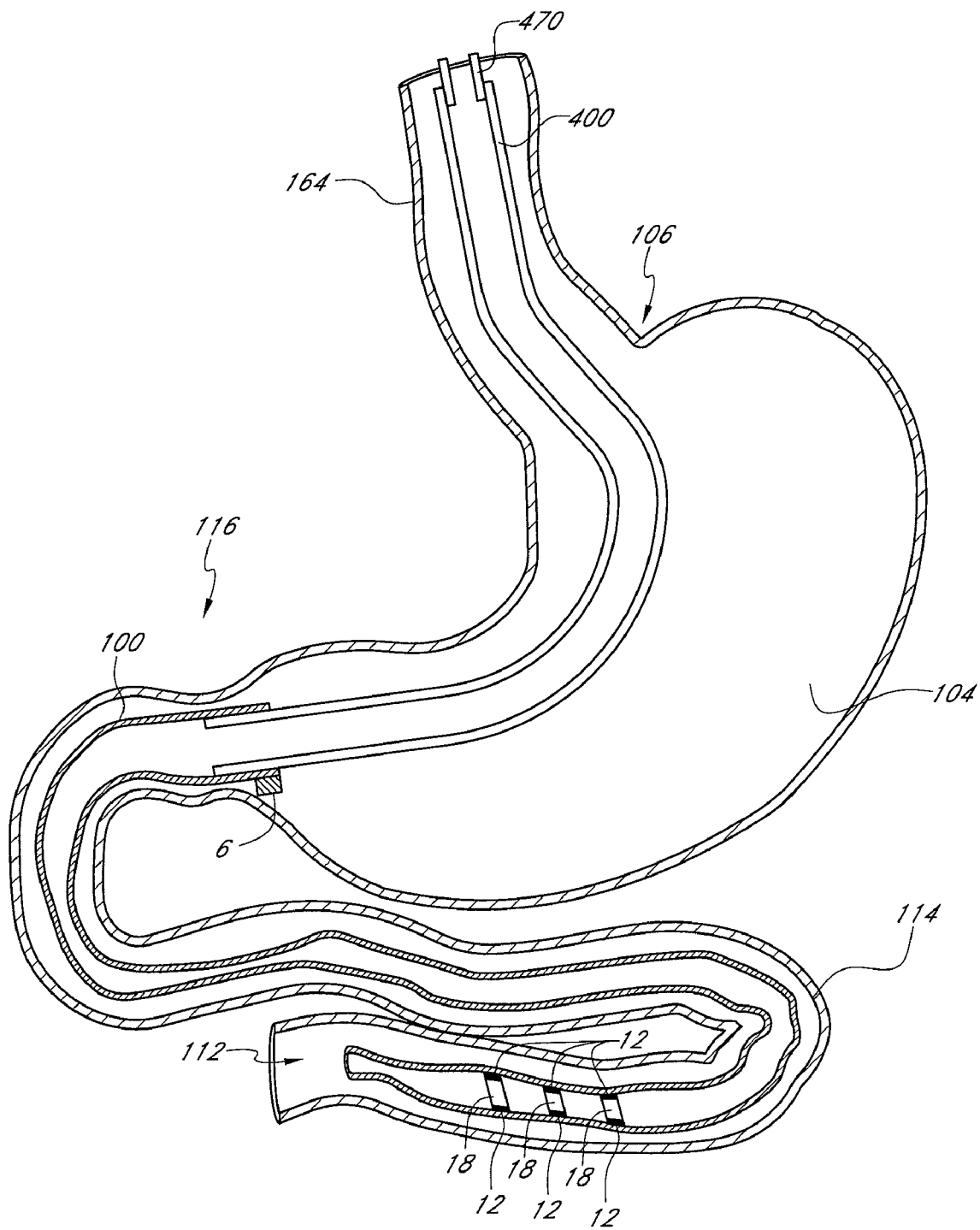

In some embodiments of the present invention, as shown in FIGS. 10A-10C, toposcopic delivery of sleeve 100 with attached electrodes 12 is achieved by performing the following steps:

Optionally attach cuff 102, if a cuff is part of the gastrointestinal stimulation system (not shown), as disclosed above, as well as, e.g., in the Dann '605 application. Base 6 of the stimulator component 3 can be held in a fixed position in a filling catheter 400, and later attached to the cuff 102 after complete eversion of the sleeve 100 in some embodiments. For simplicity, the attachment anchors for attaching cuff 102 to tissue in the vicinity of GEJ 106, as well as conductive element 10 of the electrical stimulator component 3 are not shown.

Figure 11:
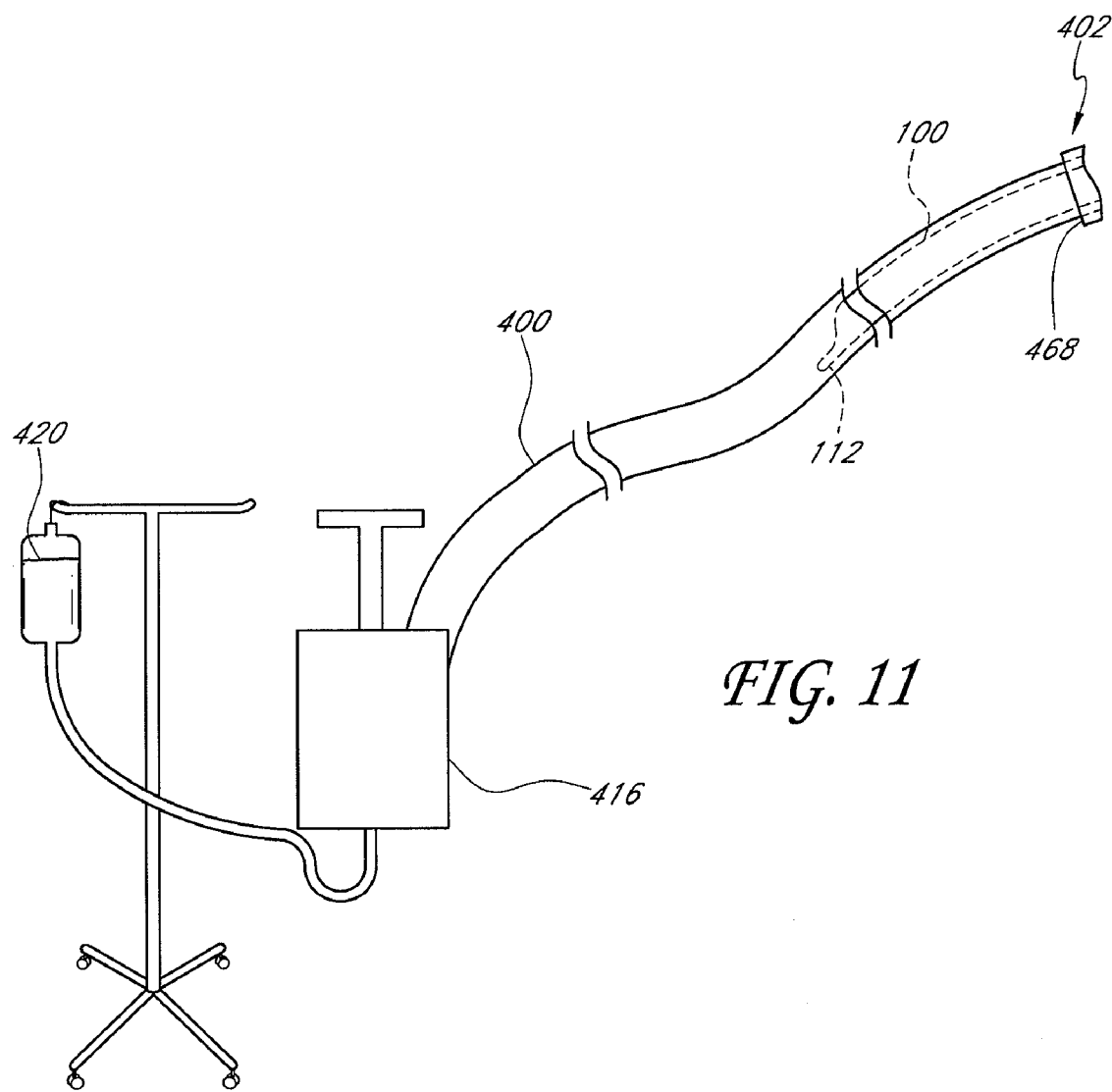
FIG. 11 schematically illustrates a system for pressurizing a toposcopically deliverable sleeve, according to one embodiment of the invention.

Place a filling catheter 400 in fluid communication with a flushing device 416 (FIG. 11).

Attach sleeve 100 that can include electrodes 12, biasing elements 16, base stimulator 6, and conductive element 10 (not shown) as described above, to filling catheter 400, invert sleeve 100 within the filling catheter, and create a fluid-tight seal 468 between the sleeve 100 and filling catheter 400, if these steps have not been previously done.

Use a sleeve grasper or advance filling catheter 400 to position distal sleeve end 154 of the undeployed sleeve 100 at or into the pylorus 116.

Flush filling catheter 400 with fluid to deploy sleeve 100, with attached electrodes 12 and optionally biasing elements 16, into intestine 114.

Confirm full placement using back pressure measurements or fluoroscopy or x-ray to detect radiopaque markers (not shown) on sleeve 100.

Attach cuff 102 (not shown) to sleeve 100.

FIG. 10A shows the proximal end of sleeve 100 and the distal end of filling catheter 400 deployed in stomach 104, with distal end 112 of sleeve 100 including electrodes 12 attached to biasing elements 18, retracted proximally within the filling catheter 400 at least as far as the esophagus 164. Also shown is stimulator base 6. Conductive element is not shown in FIGS. 10A-10C for clarity. FIG. 10B shows sleeve 100 partially unraveled or otherwise deployed such that distal end 112 has advanced past GEJ 106. FIG. 10C shows sleeve 100 including biasing element 18 and attached electrodes 12 fully deployed down intestine 114. In some embodiments, the conductive element 10 of the stimulation component 3 is operably attached to a wall of the sleeve 100 to help prevent kinking of the conductive element 10 during eversion at the time of toposcopic delivery. In another embodiment, the biasing element 18 could be placed in the sleeve 100 after toposcopic delivery. In this case, the electrodes 12 and conductive element 10 would be built into the wall of the sleeve 100 and could add very little stiffness to the construct to help facilitate toposcopic delivery. The sleeve 100 may have a lumen built into or attached to the wall of the sleeve 100 that runs underneath the electrodes 12. After toposcopic delivery, a biasing element 18 with a preformed shape could be inserted into the lumen and it would then help bias the electrodes 12 outwards towards the wall of the lumen. One example of this would be a helical lumen in the wall of the sleeve 100 underneath the electrodes 12. The biasing element 18 could be, in one embodiment, a nitinol wire shaped to form a helix. The temperature of the wire could be lowered before insertion to make the wire as flexible as possible. When the wire rewarms to the ambient temperature in the lumen it would re-form its biased shape.

Sleeve 100 can be inverted one or more times to create multiple layers of sleeve that unravel during toposcopic delivery. For example, a sleeve 100 can have two, three, four, or more inversions. In preferred embodiments, sleeve 100 is inverted once.

FIG. 11 illustrates a method of using a filling catheter to facilitate toposcopic delivery. As shown, filling catheter 400, such as a catheter described in the Dann '605 application, is placed in fluid communication with a device 416 that flushes filling catheter 400 with inflation media such as a fluid. Device 416 can comprise, for example, an electronic or hand-actuated piston or plunger, hand pump, impeller pump, or peristaltic pump. In some embodiments, an endoscope can flush filling catheter 400 with fluid. Device 416 can in turn be placed in fluid communication with a fluid source 420. For example, device 416 can be in fluid communication with a container 420 that holds fluid. Container 420 can hold volumes of fluid ranging from 0.25 liters to 15 liters. In preferred embodiments, container 420 holds between one and five liters. Device 420 can flush fluid through filling catheter 400 at a rate ranging from 5 cc to 100 cc per stroke or actuation of device 420. In preferred embodiments, device 420 flushes fluid through filling catheter 400 at a rate of 30 cc to 300 cc per stroke. Optionally, the filling catheter 400 or the device 416 can have a pressure or volume measurement device to measure the pressure or delivered volume of fluid that is used to evert the sleeve 100. This can be used as an alternative way to determine when the sleeve is fully deployed. The volume measurement can be used to determine when enough fluid has been delivered to fully deploy the sleeve 100. The pressure measurement can be used to detect the pressure drop once the sleeve is fully deployed and the distal end 112 of the sleeve opens up to allow the fluid to pass through with less back pressure.

Figure 18A:
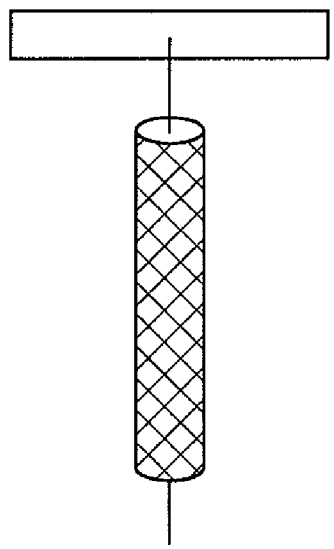
Figure 18B:
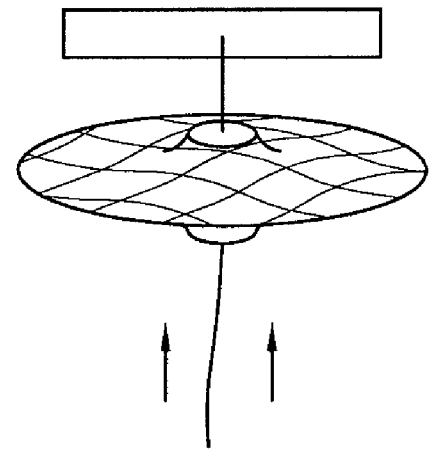

In one embodiment, filling catheter 400 passes into the lumen of sleeve 100 and a fluid-tight seal 468 is created between the proximal end of sleeve 100 and filling catheter 400, as shown in FIG. 11. In an alternate embodiment, the distal end 112 of sleeve 100 passes proximally into the lumen of filling catheter 400, the proximal end of sleeve is concentrically positioned over the distal end of filling catheter 400, and a fluid-tight seal 468 is created between the proximal, inverted, outer surface of sleeve 100 and the distal end of filling catheter 400, as shown in FIG. 18. Tubing 470 can be utilized to provide a passageway between filling catheter 400 and device 416. In this embodiment, a temporary barrier 466 can be created at distal end 112 of sleeve 100. In preferred embodiments, temporary barrier 466 is created by collapse of distal end 112 caused by the influx of fluid through filling catheter 400. In other embodiments, distal end 112 can be blocked with an absorbable or degradable plug comprising cellulose, sugar-based substances, PLA, and any other materials as would be contemplated by those skilled in the art. Any of the techniques discussed above can also be used to create temporary barrier 466.

Many advantages are associated with toposcopic delivery of electrodes 12 attached to a sleeve 100. Toposcopic delivery allows sleeve 100 to be delivered without moving electrodes 12 on sleeve 100 over and against the endothelium of the esophagus, stomach, and intestines. Sleeve 100 when delivered toposcopically can navigate tortuous anatomy. When sleeve 100 is delivered toposcopically, inverted portions of sleeve 100 deploy an axial elongation without axial sliding against the tissue such that there is no tissue abrasion and no kinks or twists are created in sleeve 100. Toposcopic delivery of electrodes 12 also requires minimal instrumentation development. The sleeve 100 delivered toposcopically is not limited to being attached to the cuff at the GEJ. The method of delivering an intestinal sleeve with a toposcopic delivery technique as described above can be used to attach a sleeve to the pylorus, the duodenal bulb, the lower portion of the stomach or anywhere else where it is deemed to be clinically beneficial.

Methods of insertion and retrieval of a gastrointestinal stimulation system including a sleeve are also described in, for example, the Dann '605 application and the Kagan '634 application. In addition to the methods described therein, a GI sleeve containing electrodes 12 can be inserted and/or retrieved using a flexible endoscope. A skilled GI endoscopist can "drive" a special endoscope (an enteroscope) through the duodenum and deep into the jejunum. Because of its small size, a pediatric colonoscope can be used to access an area further down the intestine. With proper interfacing structure on a GI sleeve, the sleeve can piggyback on the endoscope as it is driven into the jejunum and then released with its distal end left in the jejunum when the endoscope is retracted and removed from the body. This can be accomplished perorally either before or after attachment of the proximal end of the sleeve to tissue or to a cuff at the GEJ 106 or some other clinically desirable location.

Toposcopic Delivery Without Retaining a Bypass Sleeve

In some embodiments, as disclosed in the Dann '862 provisional application incorporated by reference in its entirety, all or part of the stimulation system may be delivered toposcopically without retaining a bypass sleeve within a body lumen after completion of the procedure. The delivered device may be an electrical stimulation component or any part thereof, such as one or more electrodes, or an alternative access system such as a guidewire or rail. The delivered device may be detached at the delivery site and left in place (an implant) or removed from the body following the diagnostic or therapeutic procedure.

Figure 12A:
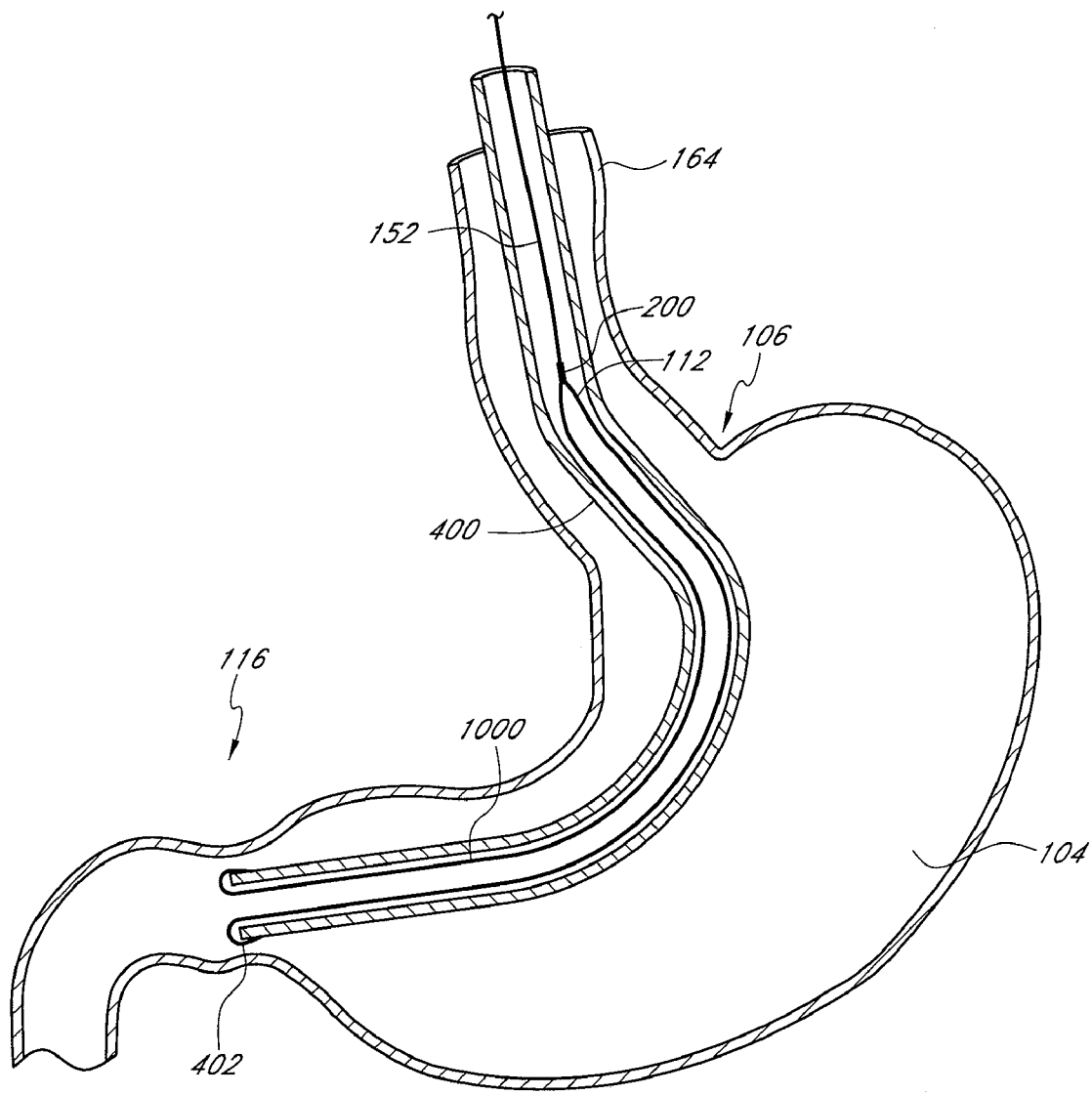
FIGS. 12A-B illustrate a toposcopic deployment system that can be used to deliver a gastrointestinal stimulation system, according to some embodiments of the invention.

Referring to FIG. 12A, there is illustrated a toposcopic delivery device in accordance with the present invention. The delivery device includes a filling catheter 400, illustrated as extending across the stomach such that a distal end 402 is in the vicinity of the pylorus 116. A toposcopic delivery sleeve 1000 (which can, in some embodiments, be essentially the same as a bypass sleeve 100 except removed after the procedure) may be is proximally retracted within the filling catheter 400.

Figure 12B:
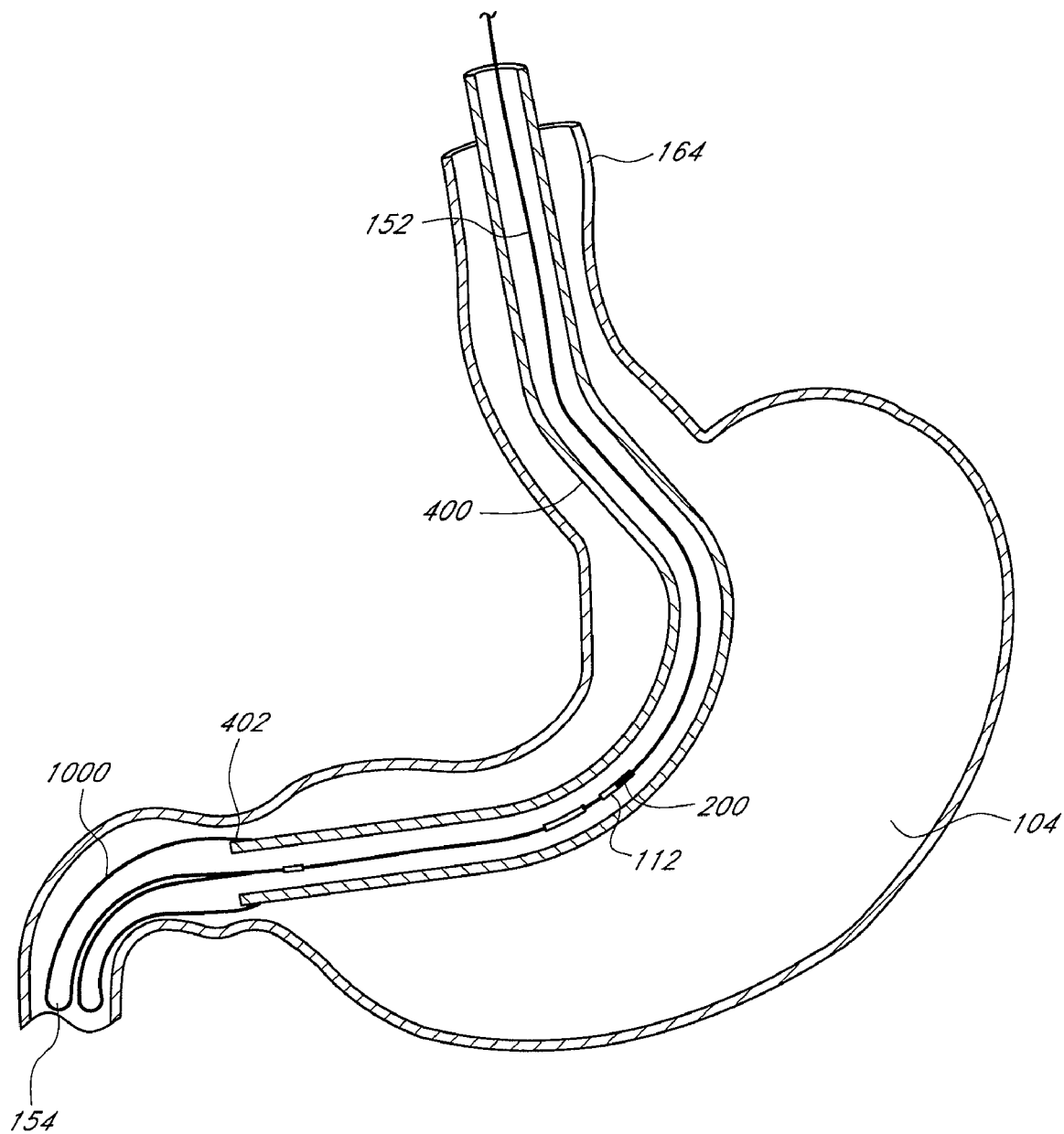

The distal end 112 of the toposcopic sleeve 1000 is closed, and provided with a connector 200. As illustrated in FIG. 12B and as will be apparent in view of the preceding discussion, the connector will advance distally in response to the introduction of inflation media through filling catheter 400.

The connector 200 may be removably or permanently connected to a device, such as, for example, a base stimulator, a biasing element, a conductive element, or an electrode, which may be a wireless electrode. In FIG. 12A, the connector 200 is connected to a guidewire 152. As the sleeve 1000 is everted distally, the connector 200 advances distally, pulling guidewire 152 in a distal direction. In this manner, a guidewire 152 may be distally axially advanced through a tortuous pathway, within the sleeve 100.

Following complete eversion of the sleeve 1000, the connector 200 may be caused to release the guidewire 152. Release may be accomplished in any of a variety of ways, such as by introduction of a solvent through sleeve 1000, introduction of a solvent around the outside of the filling catheter 400, thermally releasing a polymeric link through the use of a monopolar or bipolar electrical circuit as is understood in the detachable intracranial aneurysm coil field, or the like. Alternatively, the guidewire 152 may comprise a hollow outer sleeve which axially slideably receives an inner core. Axial, proximal or distal displacement of the core with respect to the sleeve can be utilized to detach the connector 200. The guidewire may also be forceably detached, by a pushing, twisting or pulling motion.

Following detachment of connector 200 and opening of the distal end of the sleeve, the sleeve 1000 may be proximally retracted leaving the guidewire 152 in place. Alternatively, devices may be advanced along the guidewire 152 through the sleeve 1000, leaving the sleeve 1000 in position.

Additional Fastener Embodiments

A stimulation system as disclosed herein can be attached to the wall of the GI tract with any variety of fasteners known in the art. In some embodiments, a stimulation system is securing using fasteners disclosed in the Kagan '634 application, and discussed below.

Figure 13A:
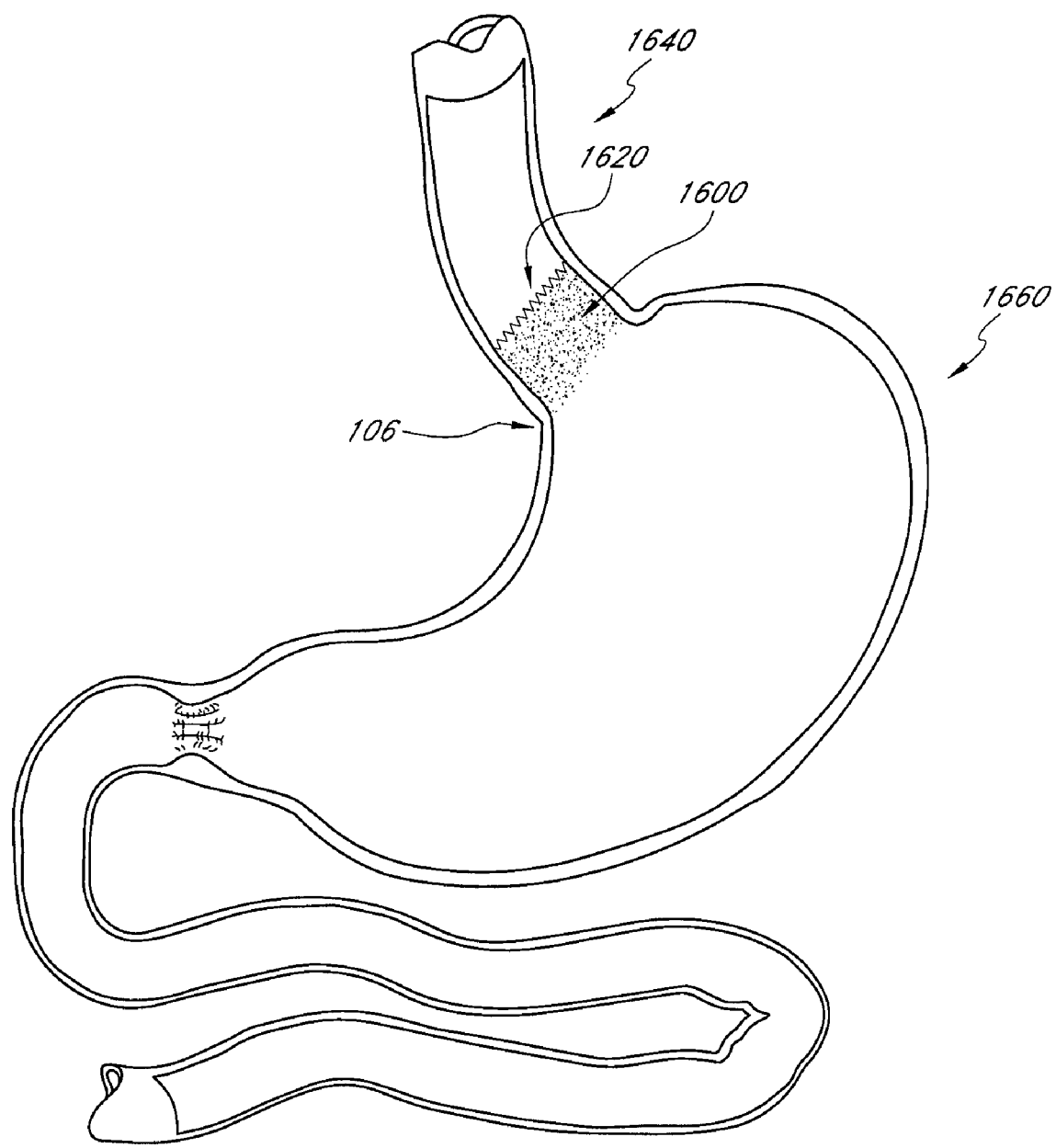
FIG. 13A illustrates a possible attachment site for a gastrointestinal stimulation system, according to some embodiments of the inventions.

The present inventors believe that some areas of the esophageal or gastric wall exhibit physical properties more conducive to retaining attachment structures than other areas. For example, an attachment zone 1600, shown in FIG. 13A, directly below the squamocolumnar junction (SCJ) 1620, also known as the Z-line, ora serrata, and mucosal gastroesophageal junction (GEJ) 106, may be such an area. The SCJ marks the junction of the squamous mucosa of the esophagus and the columnar or glandular mucosa of the stomach. The SCJ is typically located at or above the GEJ.

At least a portion of a gastrointestinal stimulation system may, in one preferred embodiment, be attached in an attachment zone 1600 no more than about 2 cm and preferably no more than about 1 cm below the SCJ 1620 and below the esophagus 1640 where the tissue wall thickness is thicker than the tissue wall thickness of the esophagus 1640 and where there exists a serosal outer surface not exhibited at the esophagus 1640. The device is also preferably attached at a location in the attachment zone 1600 so as to minimize the risk of reflux. The SCJ 1620 can be located relative to other anatomical regions. It normally may be found at the GEJ 106. The GEJ 106 is the region at which the tubular esophagus joins the saccular stomach. The GEJ 106 can be considered the first part of the stomach 1660 or the cardia and is located at the proximal margin of the longitudinal gastric mucosal folds or in the distal 2 cm of the esophagus 1640 and proximal stomach 1660. Endoscopically, the location of the GEJ 106 can be approximated by identifying the proximal margin of the gastric folds.

Due to patient to patient variability, as well as a variety of medical conditions, the anatomical relationships described above are not always found in all patients. For example, the location of the SCJ relative to the GEJ varies naturally patient to patient as well as due to certain medical conditions such as Barrett's esophagus.

Thus, a first aspect to the location of attachment of the devices disclosed herein relates to the position of the attachment structures along the axis of the hollow lumen or organ. As described above, the attachment location in the axial direction is preferably in the vicinity of the gastroesophageal junction, and particularly just below the SCJ. This attachment site can be located endoscopically by observing the color change which occurs at the SCJ, and advancing or positioning the attachment structures of the endoscope slightly below that line.

In some clinical situations the gastroesophageal junction, or GEJ 106, is a preferred attachment point for, for example a portion of a gastrointestinal stimulation system such as a gastroesophageal sleeve 100 or a stimulator base housing 6 as discussed above. Attachment at the GEJ 106 excludes all gastric secretions from the interior of the gastrointestinal sleeve device to separate ingested food and liquids in the sleeve device from all digestive secretions. The gastroesophageal junction is one of the preferred attachment sites because the tissue wall is relatively thick at this location and it is relatively easy to access via a peroral route. More specifically, the area directly below the squamo-columnar junction (a zone of tissue that is considered to be at or slightly above the beginning of the GEJ 106) is currently thought to be the best place to attach a device, for example using T-tags, sutures or other fasteners.

A second aspect to the location of the attachment structure relates to the depth within the adjacent tissue wall (i.e., in a transverse direction to the longitudinal axis of the esophagus described above) within which the various anchors or retention structures disclosed herein reside. Applicants believe that the location in the transverse direction is subject to migration or other change post-implantation, as described in connection with FIGS. 13B through 13D.

Figure 13B:
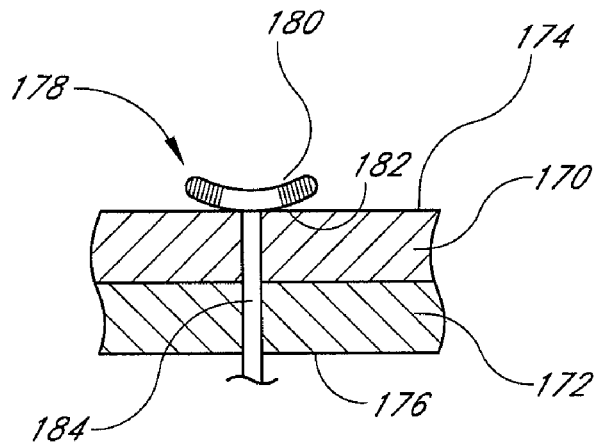
FIGS. 13B-13D illustrate a possible model of tissue ingrowth following transmural T-tag implantation, according to some embodiments of the invention.

Referring to FIG. 13B, there is disclosed a highly simplified schematic cross sectional view of a tissue wall such as the wall of a hollow organ or lumen in the body, including the wall at the vicinity of the gastroesophageal junction. The tissue wall comprises a serosa 170 and a muscularis 172. Additional tissue layers have been omitted for simplicity. In general, as is appreciated by those of skill in the art, the serosa 170 is on the outside of or faces away from the stomach, and the muscularis is on the inside, or faces towards the interior of the stomach. The serosa 170 thus includes a serosal surface 174 which faces away from the interior of the stomach, and the muscularis 172 includes a muscularis surface 176 which faces towards the interior of the stomach.

Figure 13C:
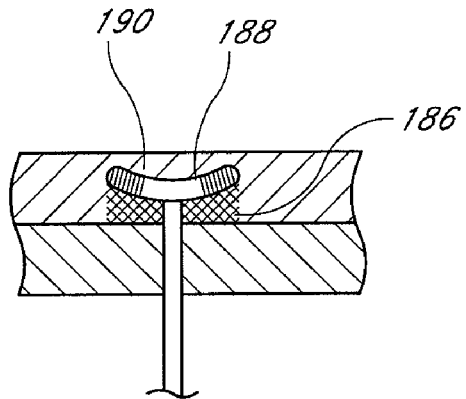
Figure 13D:
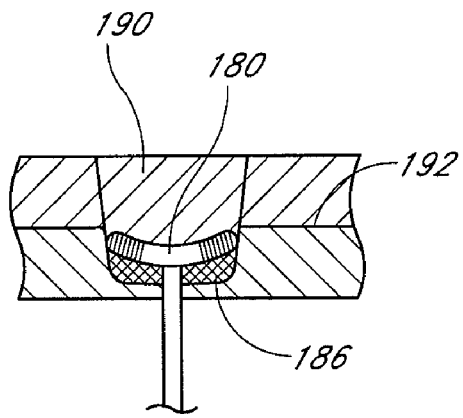

An attachment device or anchor 178 is illustrated in part in FIGS. 13B through 13D. The attachment device 178 can take any of a variety of forms, described elsewhere herein. In general, the attachment device 178 includes a retention element 180 having at least one retention surface 182 thereon. The retention element 180 may be integrally formed with or attached to a tension element 184, which extends through the tissue wall and is secured to the device implanted within the gastrointestinal tract. Although the attachment mechanisms disclosed herein will be defined primarily in the context of an obesity device, which is attached in the vicinity of the GEJ 106, those of skill in the art will appreciate that the attachment system disclosed herein may be utilized in any of a wide variety of other anatomical locations, such as in the bronchial tubes, urethra, ureters, fallopian tubes, throughout the GI tract, and others which share a serosa or serosa like layer, such as in the kidney, bladder, and other organs, as would be recognized by those skilled in the art.

Referring to FIG. 13B, the retention element 180 is illustrated with the retention surface 182 residing against the serosal surface 174. Retention surface 182 may comprise any of a variety of forms, such as a proximal surface on a T-tag, proximal surface on a washer or disc, or any other surface which extends in a generally lateral direction with respect to a longitudinal axis of the tension element 184. The transverse retention surface 182 may be radially enlargeable or expandable from a first, reduced cross-sectional configuration to provide a low crossing profile such as for deployment through a deployment cannula, and a second, radially expanded or enlarged cross-sectional profile as illustrated in FIG. 13B, to provide a retention surface 182 which will engage or interfere with tissue of the serosa 170 or muscularis 172 to resist proximal retraction of the attachment device 178 through the tissue. Transformation between the first configuration and second configuration can be accomplished in any of a variety of ways as is discussed further herein, such as by pivoting the retention element 180 about the attachment point to tension element 184, by radial expansion, by inflation, or other technique.

Tension element 184 may comprise any of a variety of connectors or elements adapted to extend through the tissue wall, such as a suture, or other single stand or multi-strand filament or material. In some embodiments the tension element 184 is formed of a polymer such as PEEK or silicone. The tension element 184 may also, in some embodiments, have elastic properties. In other embodiments the tension element 184 does not have elastic properties. By use of the term tension element, no specific mechanism is suggested, and the element is not required to be under mechanical tension.

The attachment device, otherwise sometimes referred to herein as a tissue anchor, T-tag or other label, it is illustrated in FIG. 13B in a schematic fashion as it may appear at the time of implantation. Since in certain implementations of the invention the length of the tension element 184 will exceed the uncompressed thickness of the adjacent tissue wall, the retention surface 182 may even be spaced slightly apart from the serosal surface 174 depending upon the transient motion or configuration of the stomach at any given time.

Without being limited to any particular structure or mechanism, Applicants believe that the presence of the attachment device may cause or accelerate the formation of a layer 186 of serosal tissue having increased tissue density relative to unaffected or normal serosal tissue. The layer of increased density 186 may result from a process in which the transverse retention surface 182 places pressure against the serosa 170, causing a localized necrosis due to the restriction of capillary blood flow. The necrosed tissue thereafter fibroses, as a part of a normal healing response. The layer of increased density 186 or fibrosis may also result from a foreign body reaction triggered by the presence of the transverse retention surface 182. Applicants have observed a greater degree of fibrosis or denser tissue on the side of the T-tag facing the lumen of the stomach, for example on the retention surface 182.

In certain animal trials conducted by Applicants in which the animals were sacrificed five weeks following implantation of the attachment device 178, successful anchors appeared similar to the simplified schematic illustration of FIG. 13C. In this illustration, the location of the retention element 180 has changed relative to the serosa 170 and muscularis 172, and the distal surface 188 of the retention element 180 has been covered with an overgrowth of serosal tissue 190. A fibrotic layer 186 is positioned in between the retention surface 182 and the muscularis 172. Although illustrated only on the proximal side of the retention element 180 where the greatest degree of fibrosis has been found to occur, the fibrotic response appears to some extent to surround and wall off the entire retention element 180.

It appears to the present inventors that formation of a sufficient fibrotic response on the proximal side of the retention surface 182 decreases the likelihood that the attachment device 178 will relocate to the inside of the stomach under normal agitation of the stomach, changes in the thickness of the stomach wall, and other conditions normally occurring in the stomach. A similar response is schematically illustrated in FIG. 13D, in which the layer 186 of high density serosal tissue remains on the proximal side of the retention element 180, however one or both of the layer 186 and retention element 180 have relocated to below the normal plane 192 separating the serosa 170 from the muscularis 172 and will remain there.

It appears to the present inventors that if the device design and/or retention element 180 design are such that in normal use the retention element 180 relocates to a position in the muscularis 172 and past the serosa 170 before a sufficient fibrotic response, the retention element 180 may relatively easily pass through the muscularis 172 and failure will result. Thus, it may be desirable in certain implementations of the invention to facilitate or accelerate the formation of the fibrotic layer 186. This may be accomplished in any of a variety of ways which will be appreciated by those of skill in the art in view of the present disclosure, such as by the introduction of an active agent which will trigger a fibrotic response. Suitable active agents may include any of a variety of growth factors, and/or chemical sclerosing agents which are well known for other medical applications. The surfaces of the retention element and tension element may also be provided with an anti-bacterial characteristic, such as by eluting an antibiotic agent, or having a bacteriostatic or bacteria inhibiting coating. Drug eluting coatings are well understood in the coronary stenting arts, and can be adapted for use in the present context by those of skill in the art.

Active agents may be applied as a coating to the retention surface 182 or retention element 180, or may be impregnated into the material of retention element 180 and/or tension element 184, such as to permit a timed release into adjacent tissue. Incorporation may be accomplished by loading the active agent into tortuous pathways or pores exposed to the surface of the retention element 180, or by inclusion in a bioabsorbable or bioerodable carrier attached to or positioned in the vicinity of the retention surface 182. Energy sources may also be utilized, such as to generate heat or otherwise stimulate formation of a fibrotic response, as is discussed further below. Formation of the fibrotic layer 186 may also be facilitated by mechanical means, for example, in one embodiment, by roughening the retention surface 182 with the addition of fibrotic layer enhancement structures such as a plurality of bumps or etched lines.

Figures 13E, 13F:
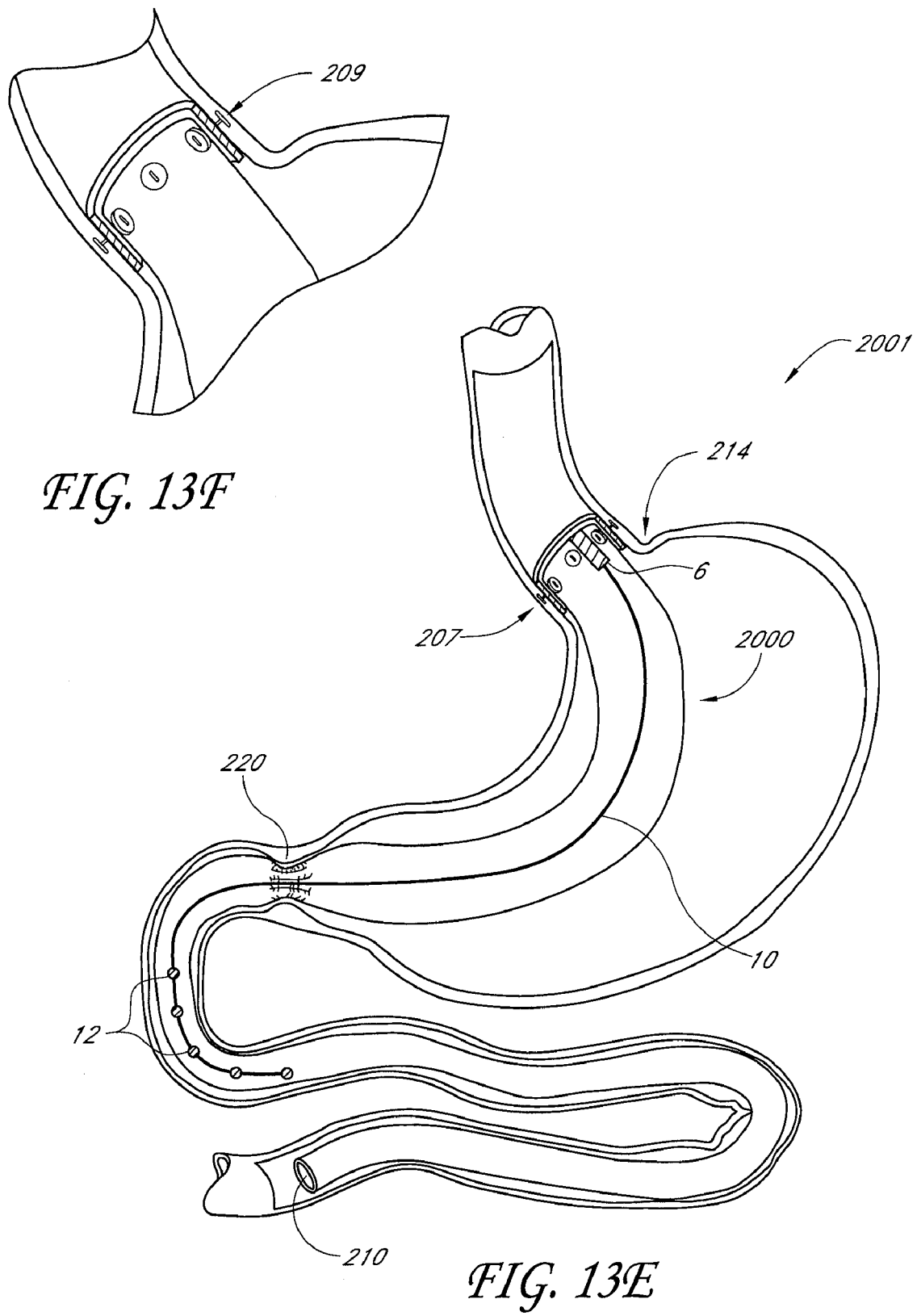
Figure 17A:
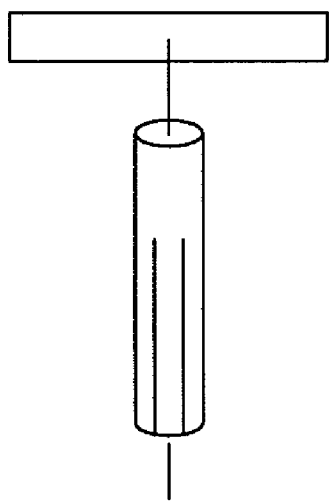
Figure 17B:
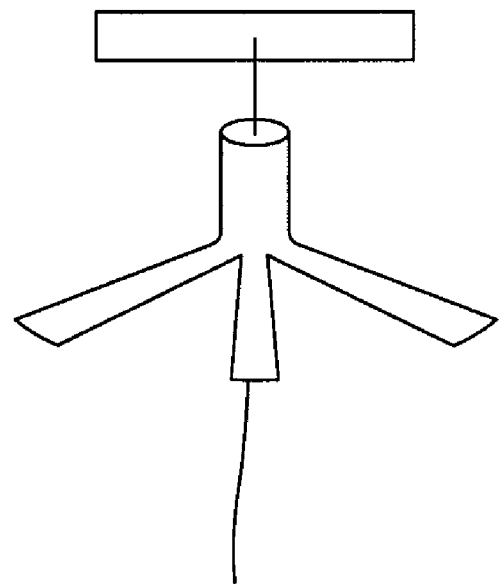

FIG. 13E shows an implanted gastrointestinal stimulation system 2001 including a sleeve 2000 attached by an attachment cuff 214 with the use of T-tags 207. Also shown schematically is stimulator base housing 6 operably attached to cuff 214, as well as conductive element 10 and electrodes 12 as previously described. FIG. 13F is an enlarged view of the attachment cuff 214 attached with T-tags 207 showing the transverse retention elements 209 of the T-tags 207 embedded in the stomach wall, as may be observed several weeks post implantation. Elements of the stimulator are not shown in FIG. 13F for clarity.

T-tag type fasteners can be used endoscopically to attach many of the structures described herein. A T-tag is basically a retention element 180 in the form of a cross member or "T" that is attached to a tension element 184 in the form of an elongated member or tail at or near the mid-point of the T. A "stem" may be a structure at the joining point of the T and tail. From the perspective of a peroral attachment technique, in which the attachment devices are preferably advanced through muscularis 172 in the direction of the serosa 170, the stem or tension element will be referred to herein as relatively proximal to the cross member on the T-tag. The T-tag is a member of a more general family of tissue anchors, in which a proximally facing surface 182 (such as the proximal surface of the cross member) is adapted to be bent, folded, or otherwise reduced in crossing profile to a first configuration in which it can be advanced distally through a relatively small tissue opening, to a second configuration in which it presents a proximal serosal surface contacting area for resisting proximal retraction through the access pathway. Thus, although described primarily in the context of a T-tag and variations thereof, the present invention relates more broadly to tissue anchors of the type for presenting a retention surface which may have any of a wide variety of configurations. Some are described in additional detail below. The stem may also be referred to herein as a tension member, and may comprise a suture, or other single strand or multi-strand element for drawing the tissue anchor against the serosal tissue and/or connecting the tissue anchor to the implantable cuff or other endolumenal implant.

T-tag fasteners are generally configured to flex or pivot at the juncture of the T and tail to allow delivery along the axis of the T through a minimal puncture diameter. T-tag fasteners can be configured with an extended tail that may extend out the mouth and optionally be used to parachute devices for attachment into position in vivo. Other T-tag configurations can include, crimp, snap, screw or other means of securing the T-tag tail when appropriate. One embodiment of a T-tag fastener could include a dual tail. Such a dual tail could be combined with extended tails that could then be tied out side the body with the ensuing knots then tightened within the body. Such a dual tail could be constructed of one of a number of non-biodegradable suture materials known in the art including polypropylene, nylon, braided Dacron or silk. In some clinical situations biodegradable tails could be indicated and could be constructed using materials described herein. In a preferred embodiment the tails could be constructed of a monofilament material.

In certain implementations of the present invention, it may be desirable to increase the effective surface area of the retention surface 182. This may be accomplished using any of a variety of disc or button shaped attachment devices 178 disclosed herein, or by introducing a buttressing component or element in the nature of a washer or other structure for enlarging the effective surface area. This buttressing structure may sometimes be referred to herein as a pledget. The buttressing material is generally configured perpendicular to the axis of the tension element 184 (e.g. suture, rivet or staple) and therefore best distributes forces along the axis of the attachment means.

T-tags or other serosal anchors can be delivered through a hollow needle type delivery system (e.g. T-ANCHOR INTRODUCER GUN (Moss, Moss Tubes)) that has been redesigned/modified so it can be passed through the working channel of an endoscope. A T-tag can be provided with an elongated tail that can extent out through the mouth and be used to parachute structures into place in-vivo.

In one embodiment the T-tags are placed such that the sutures of the T-tags could be knotted outside of the body and the knots could be pushed down the working channel or outside of the working channel of the scope until positioned to retain the cuff. The suture tails could subsequently be removed. To facilitate management of all the suture tails, two T-tags could first be placed to secure the cuff followed by placement of the rest of the T-tags. In a preferred embodiment the T-tag tension elements, such as tails, sutures, or other structures as described herein, would terminate in the stomach, such as by tied knots, sliding buttons, or preexisting terminated ends, such that they would not need to be brought outside of the body.

As an alternative to tying sutures outside of the body, any of a variety of suture locks may be utilized to secure the suture with respect to the cuff. In general, a suture lock is provided with a central aperture for moveably receiving the suture therethrough. The lock may be configured for one way advance along the suture, having a spring biased engaging element for resisting movement of the lock in the opposite direction. Alternatively, a central plug may be advanced into the central lumen, to compress the suture within the suture lock and retain the suture lock at a selected position. Any of a variety of clips may also be axially or radially moved into position, to engage the lock with the suture. The suture lock may be advanced down the suture and positioned with the desired tension against the interior surface of the cuff, and activated as necessary to lock the suture lock in place. The remaining suture tail may be severed, using conventional endoscopic techniques.

Alternatively, the suture lock may be secured to the cuff 102 such as at an aperture of the cuff, prior to implantation of the cuff 102 in the patient.

Many of the serosal anchors described herein can be formed using a single piece of Polypropylene, Nylon, PEEK, silicone, or other polymeric material well known in the art for use in construction sutures, which forms the "T" and tail as a single unit. Alternately two different materials can be combined, for example by insert molding, to achieve different properties of the "T" and tail. In another embodiment this could be combined with a "T" portion that is coated with a material selected for specific clinical properties such as encouraging or discouraging either in-growth or adhesion. The "T" portion may also be surrounded by another material such as ePTFE or Dacron graft material. "T" diameter or serosal surface contacting width can vary for example ranging from 0.5 mm to 3.0 mm in diameter for nylon or polypropylene with the typical "T" having a diameter of 1-2 mm. A tail could be the dimension of a standard suture and could generally vary from 5-0 to 0 (USP standard classification) though smaller or larger sizes may be appropriate in certain clinical situations.

FIGS. 14A & 14B illustrate a curved T-member 300 for a T-tag fastener. The convex curved tissue-contacting surface 302 of the curved T-member 300 serves to distribute the attachment force for an implanted device smoothly across the tissue to minimize any stress concentrations or higher pressure spots that could cause tissue necrosis and/or erosion. The T member 300 has a double eyelet 304 for attachment of a suture or other filament. The T-member is preferably molded of a fairly rigid, high strength biocompatible polymer such as PEEK.

FIGS. 15A-15B illustrate a T-tag fastener 2200 with a hydrogel disc 2204 that can be placed between the deployed T-member 2208 and the extragastric (serosal) surface. The disc 2204 could be delivered through the T-tag delivery needle, and unroll after passage through the needle. The hydrogel disc 2204 acts as a buttress or pledget to distribute the forces transmitted between the T-member 2208 and the extragastric surface and thereby it strengthens the attachment of the T-tag fastener 2200. The hydrogel used in FIGS. 15A-15B can optionally be replaced with alternate materials described herein for example silicone, NiTi and fluoropolymers. A Hydrogel or other buttress or Teflon pledget for a T-tag could also deploy in some other manner. The disc configuration shown can be replaced with for example, braided or woven wires or filaments that would expand/deploy after passage through the needle (FIGS. 16A-16B), a Malecot-style deployable tubular structure (FIGS. 17A-17B) or other expandable or deployable configuration (e.g. FIGS. 18A-18B). Although FIGS. 15A-15B, 16A-16B, 17A-17B, and 18A-18B illustrate T-tag fasteners, such as 2200 in FIGS. 15A-15B used with T-members 2208, uses of the T-tag fasteners without T-members and just with the hydrogel disc 2204 of FIGS. 15A-15B or the woven filaments, Malecot-style tubular structure, or the expandable structure of FIGS. 16A-16B, 17A-17B, and 18A-18B, respectively, are also contemplated.

In the above examples where it has been suggested that a fixed distance between the T-member and the device it is being used to attach is desirable it has been suggested that in some cases a distance greater than the thickness of the captured gastric wall may be clinically indicated. This is due to the ability/tendency/possibility that the gastric wall could react to the presence of a foreign body (the attachment structures) by thickening. In this event, in some cases, it can be clinically preferable that the preset distance accommodate some or all of this increase in wall thickness.

In some embodiments, a T-tag or T-pledget could have a discrete layer of a fabric interspersed between the T-tag and the serosal surface. This can advantageously facilitate tissue ingrowth and/or enhance transmural fastening of the device. The fabric may be woven or non-woven. The fabric may be permeable or impermeable. Depending upon the desired performance, the fabric material may be one or more of: Dacron, Dulex Mesh (Bard), Dual Mesh (Gore), PTFE (Teflon), ePTFE, plastics such as polyvinyl chloride, polyurethanes, polypropylene, polyesters, silicons, fibrin glues, extracellular collagen matrix materials such as Veritas (from Synovis) or Durgen Plus (from Integra), Goretex (Gore), silver composites, silver alloys, or any other suitable material referenced in the present disclosure. Any of the above materials can be impregnated or coated with a silver compound such as silver nitrate or silver oxide depending on the desired clinical result.

Referring to FIGS. 19A-19D, retention elements 920 are designed for expandability. A T-tag or T-fastener can be used to provide knot free means to retain a suture against pull through of an associated anatomic structure. A further advantage of a T-tag is that the forces applied to the suture tail of the "T" are distributed over a larger area than a single stitch. This is accomplished by using a "T" dimensioned with a width wider than the diameter of the suture and a length longer than a typical bite or stitch. A disadvantage of a T -tag is that insertion of a T-tag through tissue potentially requires a hole many times, for example 5-15 times, the diameter of the suture tail.

Figure 19A:
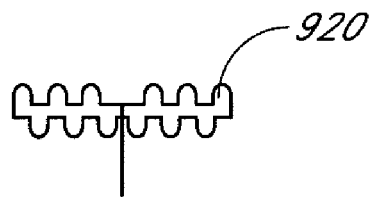
Figure 19B:
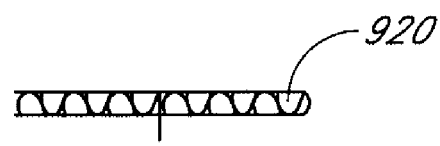
Figure 19C:
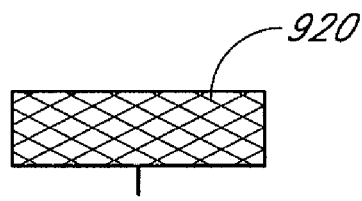
Figure 19D:
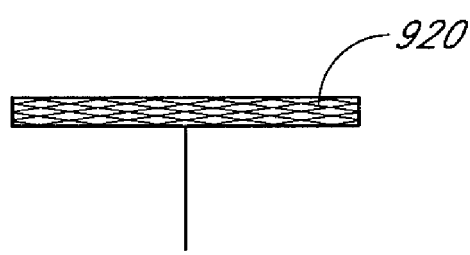

To deliver an improved buttressing capability in a T-tag fastener or T-pledget with a minimum delivery hole it is beneficial to use a "T" or pledget designed to expand after delivery. This can be beneficial in many clinical situations. In addition to rolling or compressing, alternate structures can include materials that expand when exposed to water such as hydrogels. FIGS. 19C and 19D show how a T-pledget 920 or T-tag of woven cylindrical meshes that may be compressed or elongated to achieve a reduced diameter and expanded or shortened to become wider. Compared to a rectangular sheet, alternate configurations of a rolled and unrolled sheet can achieve a T-pledget 920 or T-tag with increased projected width relative to its rolled diameter through the use of matching cutouts, as shown in FIGS. 19A and 19B. Though not as efficient in diameter-to-projected width ratio, is some cases it may be clinically desirable to have a "T" that is in a circular shape.

To resist bending perpendicular to the axis of the suture, it may be beneficial to use metals, for example Ti, SS or NiTi. In some clinical situations, encapsulating or coating the metal with a fluoropolymer or other coatings as described herein may also be beneficial.

T-tag with inflammatory reaction or other additives—The pledget material could be optionally coated or impregnated with materials and/or medicaments as described herein. For example the pledget can be coated with a material that would enhance inflammation and scar formation. Alternatively, a coating or medicament that would either encourage or discourage in-growth can be applied.

In some clinical situations it may be beneficial to use both these types of coatings. For example, though inflammation can lead to scarring fibrosis and ultimately strengthen tissue, the inflammatory process initially results in tissue weakening that can include tissue liquefaction. Therefore, it can be desirable that a fastener that induces an inflammatory response for long term strength also include means to support the tissue during the weakened stage.

Inflammatory reaction materials would be limited to a portion of the T-tag or T-pledget as the inflammatory response weakens tissue before the scarring fibrosis occurs. Therefore, for example, having the area at the center of the T or pledget with this inflammatory material and the ends of the "T" without this material could have an optimized balance of short term and long term strength.

Drug-eluting coatings may be used to encourage or discourage tissue ingrowth into the fasteners or other device attachment mechanisms described herein. A low inflammatory response is generally desirable for encouraging tissue ingrowth. Anti-inflammatory drugs that may be used include steroidal anti-inflammatory drugs, e.g. prednisone, and non-steroidal anti-inflammatory drugs (NSAID), e.g. chromalin. Conversely, drugs that may be used to control or reduce tissue ingrowth include Taxol (paclitaxel) (Bristol-Myers Squibb) and Sirolimus (rapamycin) (Wyeth-Ayerst Laboratories).

Embodiments designed for improved erosion resistance— The purpose of the "T" or other retention element is to distribute and resist the forces that could act to pull it through tissue, in this case the gastric wall. To better achieve this result the "T" should resist excessive bending. Though a T-fastener is generally held parallel to the surface of the extragastric wall, at the ends of the "T" the gastric wall extends outward from the plane of the surface and the axis of the "T". In this case, the gastric wall could be at a 90-degree angle, or greater, to the ends of the "T". To reduce the potential for erosion at the end of the "T" in some clinical situations it could be beneficial for the ends of the "T" to have increased flexibility which will result in a reduction of the angle between the gastric wall and the ends of the "T". This would reduce the forces between the "T" and the gastric wall and therefore reduce the potential for erosion at the ends. Structures that could accomplish this could include tapered thickness or cross section to reduce the bending moment. Alternatively or in addition, changes in material properties such as hardness, bending modulus and/or elongation can accomplish the same result. For example the "T" near the stem could be of a material of a durometer such as Shore 65 D or higher and the material may change as one moves out along the arms of the "T" transitioning through 55 D/100 A to 90 A durometer or lower. Rounding, smoothing and structures that otherwise distribute forces over a larger area will also serve to reduce erosion at the ends of the "T". A circular shaped "T" may be particularly desirable to reduce erosion.

In some embodiments, the base stimulator housing 6 could be positioned on the serosal surface of the esophagus, GEJ, stomach, or intestine while the conductive element is wired through to the mucosal luminal side of the wall.

Dual-Therapy Systems for Gastric and/or Intestinal Bypass+ Electrical Stimulation In some embodiments, a system includes an endolumenal bypass sleeve as described herein in combination with any of the stand-alone electrical stimulation (pacing) devices known in the art. Conventional electrostimulation devices may be used in the practice of this invention. Such devices include, for example, those described in U.S. Pat. No. 5,423,872 (Jun. 3, 1995) (an implantable gastric electrical stimulator at the antrum area of the stomach which generates sequential electrical pulses to stimulate the entire stomach, thereby artificially altering the natural gastric motility to prevent emptying or to slow down food transit through the stomach); U.S. Pat. No. 5,690,691 (Nov. 25, 1997) (a portable or implantable gastric pacemaker employing a number of electrodes along the greater curvature of the stomach for delivering phased electrical stimulation at different locations to accelerate or attenuate peristaltic movement in the GI tract); U.S. Pat. No. 5,836,994 (Nov. 17, 1998) (an implantable gastric stimulator which incorporates direct sensing of the intrinsic gastric electrical activity by one or more sensors of predetermined frequency bandwidth for application or cessation of stimulation based on the amount of sensed activity); U.S. Pat. No. 5,861,014 (Jan. 19, 1999) (an implantable gastric stimulator for sensing abnormal electrical activity of the gastrointestinal tract so as to provide electrical stimulation for a preset time period or for the duration of the abnormal electrical activity to treat gastric rhythm abnormalities); PCT Publication WO 1998/053878 and U.S. Pat. No. 6,321,124 (Nov. 20, 2001) (implant device equipped with tines to help secure it in the appropriate location); U.S. Pat. No. 6,041,258 (Mar. 21, 2000) (electrostimulation device with improved handle for laparoscopic surgery); U.S. Pat. No. 6,510,332 (Jan. 21, 2003); PCT Publication WO 2000/061224 entitled "Gastric Stimulator Apparatus and Method for Installing"; PCT Publication WO 2000/061223 entitled "Gastric Stimulator Apparatus and Method for Use"; and U.S. Patent Publication No. 2004-0162595 A1 entitled "Method and Apparatus for Intentional Impairment of Gastric Motility and/or Efficiency by Triggered Electrical Stimulation of the Gastric Tract with Respect to the Intrinsic Gastric Electrical Activity." All of these patents, patent applications, and/or publications are hereby incorporated by reference in their entirety.

Such a dual-therapy system could be advantageous as a sleeve could be initially implanted to accelerate weight loss, while the pacer/stimulator could be retained for maintenance. The sleeve and stimulator could be both implanted in a first procedure. Once a desired clinical endpoint is reached, one of the sleeve or stimulator can be removed in a second procedure, while the other of the sleeve or stimulator retained within the body. In another embodiment, the sleeve and stimulator are implanted in separate procedures.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A gastrointestinal stimulation system, comprising:
   a gastrointestinal bypass sleeve configured to be implanted in a patient and having a length to extend distally from the gastroesophageal junction, through the stomach, and into the intestine; and
   an electrical stimulator component comprising at least one electrode, the electrode configured to stimulate the intestine, wherein the electrode is operably attached to the gastrointestinal bypass sleeve at a location spaced apart from the pylorus when the gastrointestinal bypass sleeve is implanted in the patient.

2. The gastrointestinal stimulation system of claim 1, further comprising a gastrointestinal attachment cuff having a tubular body, a proximal end and a distal end.

3. The gastrointestinal stimulation system of claim 1, wherein the electrical stimulator component further comprises a circuit board, a battery, and a conductive element.

4. The gastrointestinal stimulation system of claim 3, wherein the battery is configured to be recharged using RF energy.

5. The gastrointestinal stimulation system of claim 3, wherein the conductive element is a ribbon.

6. The gastrointestinal stimulation system of claim 5, wherein the ribbon has one of a U-shaped or S-shaped cross-section.

7. The gastrointestinal stimulation system of claim 1, wherein the electrical stimulator is triggered by a sensor configured to detect one of the group selected from: pressure, temperature, pH, motion, and strain.

8. The gastrointestinal stimulation system of claim 3, wherein the conductive element is a lead wire.

9. The gastrointestinal stimulation system of claim 3, further comprising at least one biasing element operably connected to the electrode.

10. The gastrointestinal stimulation system of claim 9, wherein the biasing element is configured to increase one of the contact surface area or the contact surface time between the electrode and a lumen of the gastrointestinal tract.

11. The gastrointestinal stimulation system of claim 1, wherein the gastrointestinal bypass sleeve is at least partially inverted within itself, and adapted for eversion within the gastrointestinal tract.

12. The gastrointestinal stimulation system of claim 1, wherein at least part of the electrical stimulation component is configured to be attached to a serosal surface of a wall of the gastrointestinal tract.

13. A method of treating a patient, comprising the steps of:
   providing a gastrointestinal sleeve device having an elongate tubular body, with a proximal end and a distal end;
   providing an electrical stimulation component comprising:
      a circuit board and a battery contained within a base housing; a conduction element; and at least one electrode, the electrode being operably attached to the gastrointestinal bypass sleeve;
   positioning the gastrointestinal sleeve device in the patient's digestive tract such that the proximal end is at the gastroesophageal junction, the distal end is in the intestine, and the at least one electrode is in the intestine, spaced apart from the pylorus; and
   stimulating the intestine via the at least one electrode.

14. The method of treating a patient as in claim 13, wherein the base housing is operably attached to the sleeve.

15. The method of treating a patient as in claim 13, wherein positioning of the electrical stimulation device and the gastrointestinal sleeve device does not occur during the same procedure.

16. The method of treating a patient as in claim 13, further comprising the steps of: providing a gastric space-filling device operably attached to the base housing of the electrical stimulation component; and
   deploying the space-filling device within the stomach.

17. The method of treating a patient as in claim 16, wherein the space-filling device is a balloon.

18. The method of treating a patient as in claim 13, wherein the at least one electrode is attached along an outer surface of the gastrointestinal bypass sleeve.

19. The method of treating a patient as in claim 13, further comprising the step of attaching the proximal end of the sleeve at the gastroesophageal junction.

20. The method of treating a patient as in claim 13, wherein the proximal end of the sleeve is attached to the gastroesophageal junction via an attachment cuff.

* * * * *